(12) United States Patent
Almirall et al.

(10) Patent No.: US 11,131,634 B1
(45) Date of Patent: Sep. 28, 2021

(54) MATERIALS AND METHODS FOR FIELD TESTING OF CANNABIS SAMPLES

(71) Applicants: Jose Almirall, Miami, FL (US); Alexander Acosta, Miami, FL (US)

(72) Inventors: Jose Almirall, Miami, FL (US); Alexander Acosta, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 16/950,496

(22) Filed: Nov. 17, 2020

(51) Int. Cl.
  *G01N 21/78* (2006.01)
  *G01N 33/94* (2006.01)
  *G01N 33/52* (2006.01)

(52) U.S. Cl.
  CPC .......... *G01N 21/78* (2013.01); *G01N 33/523* (2013.01); *G01N 33/948* (2013.01)

(58) Field of Classification Search
  CPC ........ G01N 21/77; G01N 21/78; G01N 33/52; G01N 33/523; G01N 33/948; Y10T 436/142222
  USPC .......... 436/93, 164, 169, 901; 422/400, 401, 422/405, 420, 430, 69
  See application file for complete search history.

(56) References Cited

U.S. PATENT DOCUMENTS

| | | | |
|---|---|---|---|
| 4,771,005 A * | 9/1988 | Spiro | C09B 67/0079 422/400 |
| 4,806,487 A * | 2/1989 | Akers | G01N 33/94 436/93 |
| 9,267,866 B2 | 2/2016 | Almirall et al. | |
| 2016/0018424 A1 * | 1/2016 | Lucas | G01N 33/52 436/93 |
| 2016/0377512 A1 | 12/2016 | Almirall et al. | |

FOREIGN PATENT DOCUMENTS

| | | |
|---|---|---|
| EP | 0132313 B1 | 9/1991 |
| WO | 89/09395 | * 10/1989 |
| WO | 99/54739 | * 10/1999 |

OTHER PUBLICATIONS

Balbino, M.A., et al., "The Application of Voltammetric Analysis of Δ9-THC for the Reduction of False Positive Results in the Analysis of Suspected Marijuana Plant Matter." Journal of forensic sciences, Jul. 2016, 61 (4) 1067-1073.

(Continued)

*Primary Examiner* — Maureen Wallenhorst
(74) *Attorney, Agent, or Firm* — Saliwanchik, Lloyd & Eisenschenk

(57) ABSTRACT

The subject invention provides colorimetric test strips and fast screening field test kits for differentiating between cannabinoids in cannabis samples, preferably, for differentiating marijuana from other cannabis plants, e.g., hemp. The fast screening field test kit can also be used for confirming the presence of marijuana in a complex cannabis sample. The colorimetric test strips use a solid substrate (e.g., capillary microextraction of volatiles (CMV) device) for the colorimetric reaction. The non-polar nature of the CMV sorbent does not allow the reaction of FBBB and THC to spread, producing an intense red color in the presence of a plant with high concentration of THC (e.g., marijuana) or an orange color in the presence of a plant with a high concentration of CBD (e.g., hemp).

20 Claims, 27 Drawing Sheets

(56) References Cited

OTHER PUBLICATIONS

Dos Santos, N.A., "Evaluating the selectivity of colorimetric test (Fast Blue BB salt) for the cannabinoids identification in marijuana street samples by UV-vis, TLC, ESI(+)FT-ICR MS and ESI(+)MS/MS." Forensic Chemistry, 2016, 1:13-21.

Fan, W., et al., "High-efficiency headspace sampling of volatile organic compounds in explosives using capillary microextraction of volatiles (CMV) coupled to gas chromatography-mass spectrometry (GC-MS)." Anal Bioanal Chern, Mar. 2014, 406(8): 2189-2195.

Franca, H.S., et al., "Experimental and ab initio investigation of the products of reaction from Δ9-tetrahydrocannabinol (Δ9-THC) and the fast blue BB spot reagent in presumptive drug tests for cannabinoids." Forensic Chemistry, Mar. 2020, 17:100212, pp. 1-10.

Franca, H.S., et al., "Experimental and ab initio Investigation of the Products of Reaction From D9-tetrahydrocannabinol (D9-THC) and the Fast Blue BB Spot Reagent in Presumptive Drug Tests for Cannabinoids." Department of Chemistry and Biochemistry, Florida International University, Florida, USA, 2020, Electronic Supporting Information, pp. 1-42.

Hamblin, D.D., et al., "Evaluation of a New Technology for the Collection of Breath Components in the Detection of Marijuana Use." National Institute of Standards and Technology, U.S. Department of Commerce, International Forensic Research Institute, Florida International University, Miami, FL, USA, 2020, p. 1.

Jacobs, A.D., et al., "Detection of the Duquenois-Levine chromophore in a marijuana sample." Forensic Science International, 2014,239: 1-5.

Kelly, J.F., et al., "The Non-Specificity of the Duquenois-Levine Field Test for Marijuana." The Open Forensic Science Journal, 2012, 5: 4-8.

Stenerson, K., "Using Solid Phase Microextraction for Cannabis Testing." MilliporeSigma, Bellefonte, PA, Gerstel, sigma-aldrich.com/SPME, 2020, pp. 1-45.

Wiebelhaus, N., et al., "Differentiation of marijuana headspace volatiles from other plants and hemp products using capillary microextraction of volatiles (CMV) coupled to gas-chromatography-mass spectrometry (GC-MS)." Forensic Chemistry, 2016, 2:1-8.

\* cited by examiner

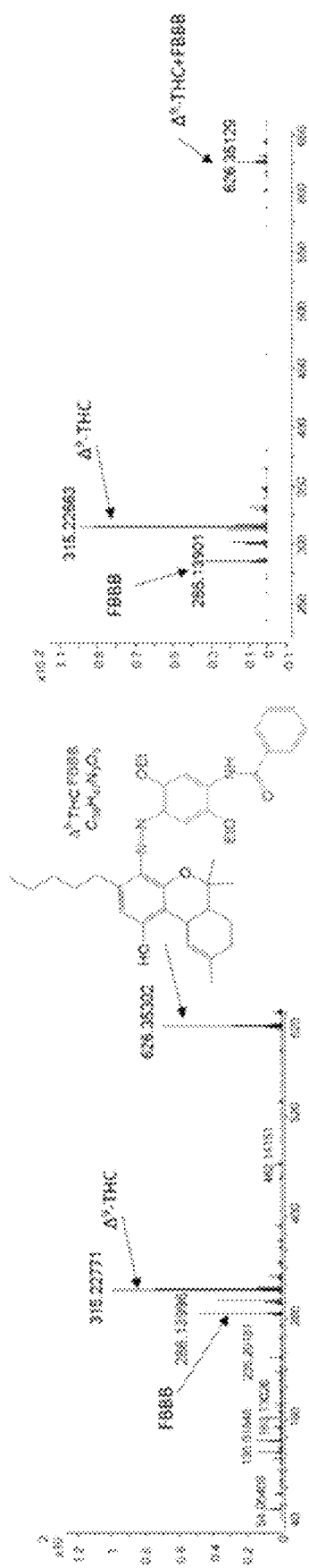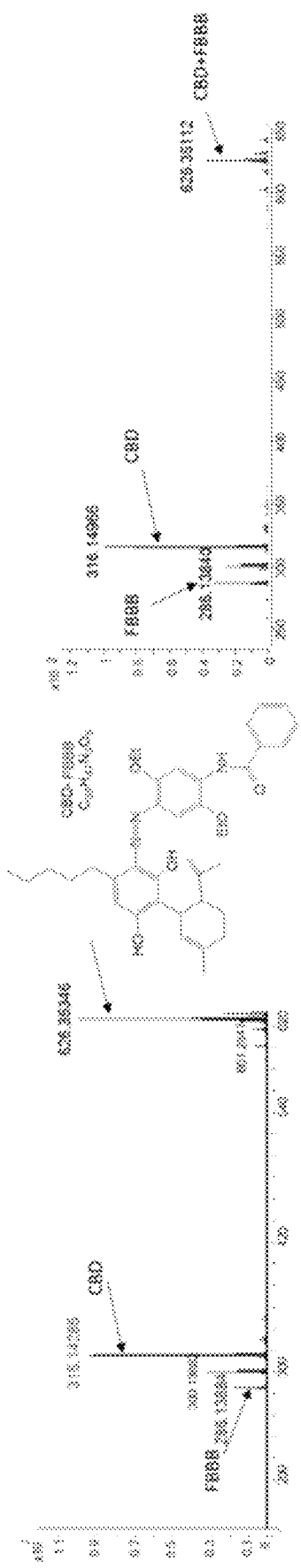
FIG. 7A  FIG. 7B  FIG. 7C  FIG. 7D

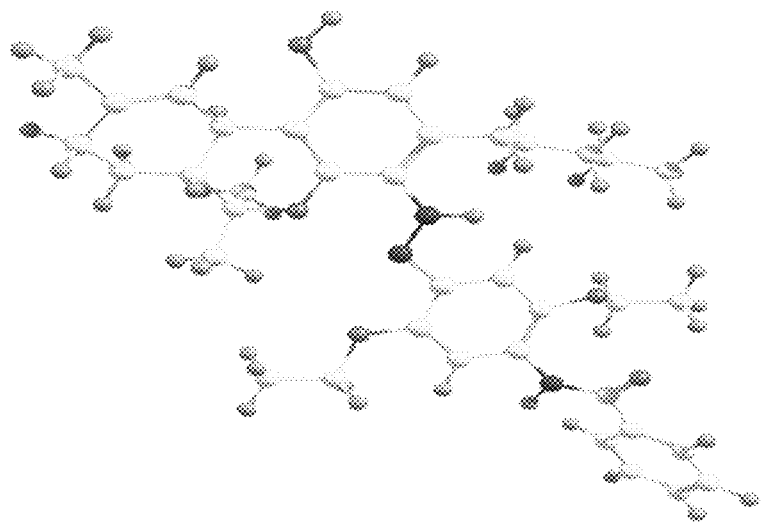
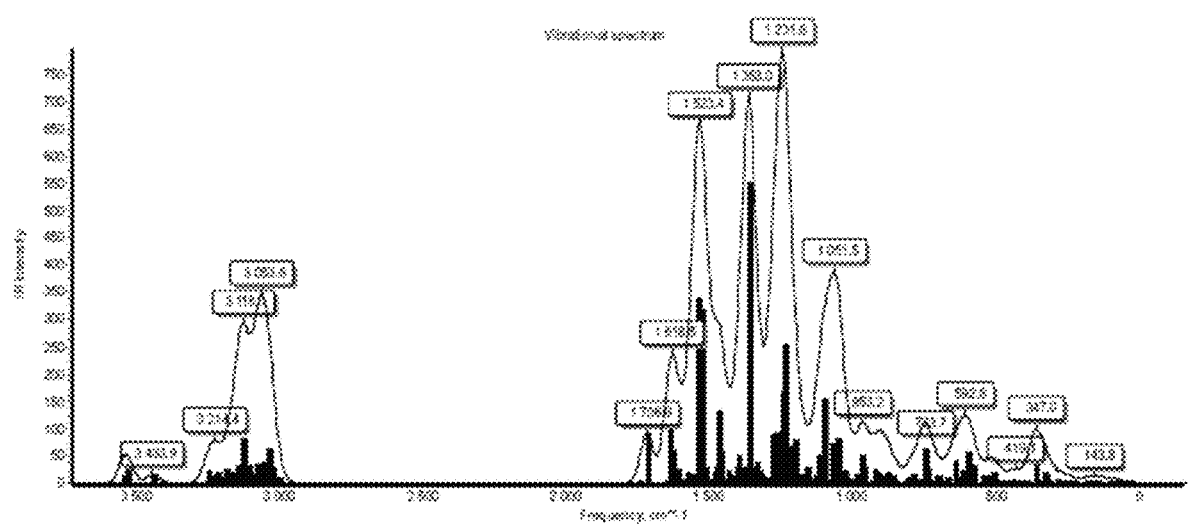
FIG. 17

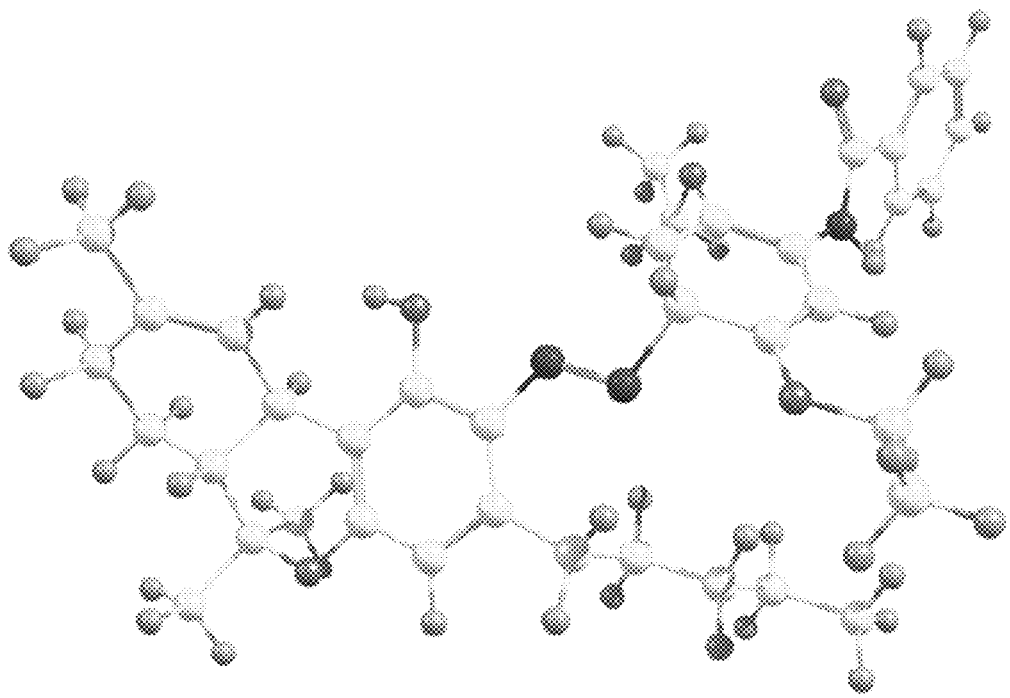
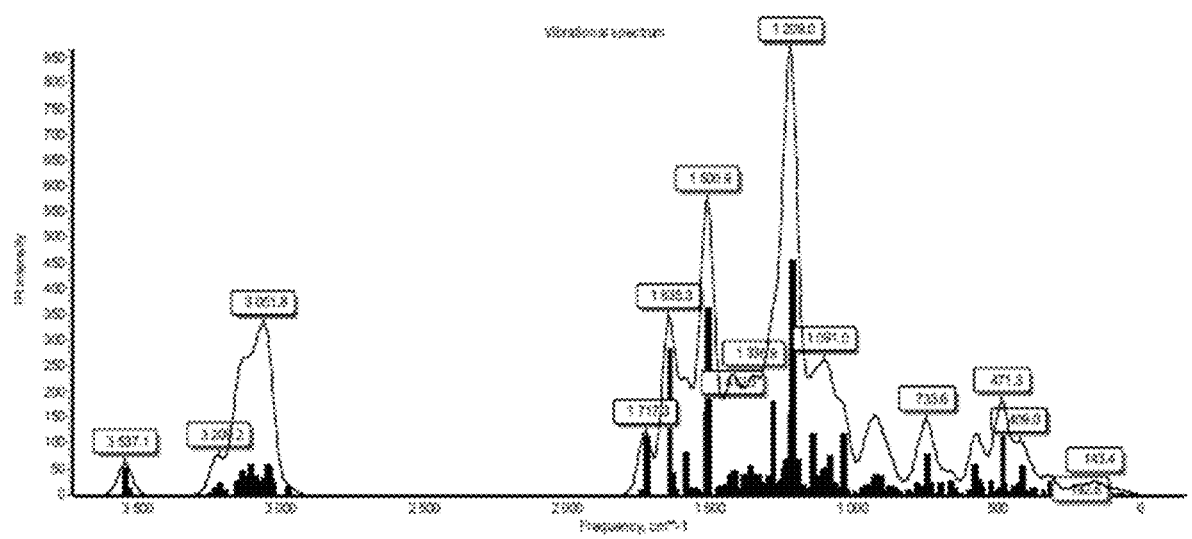
FIG. 24

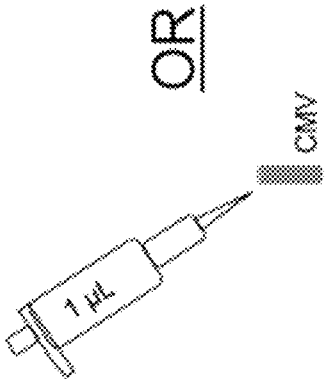
FIG. 27A
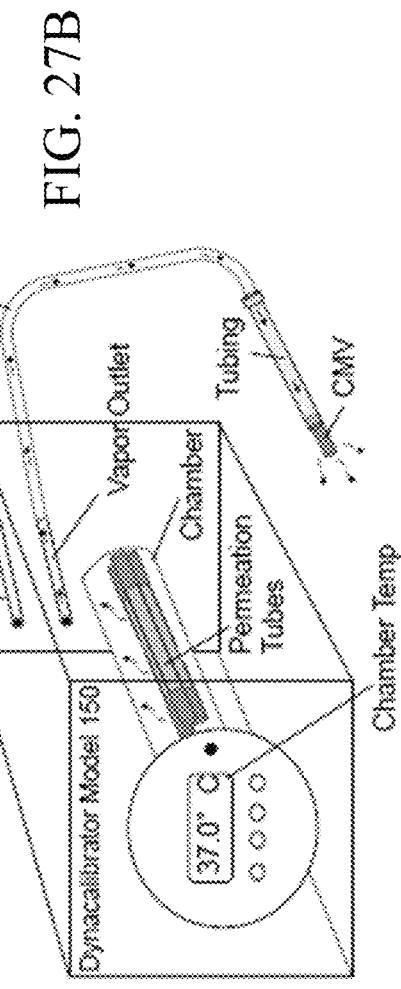
FIG. 27B
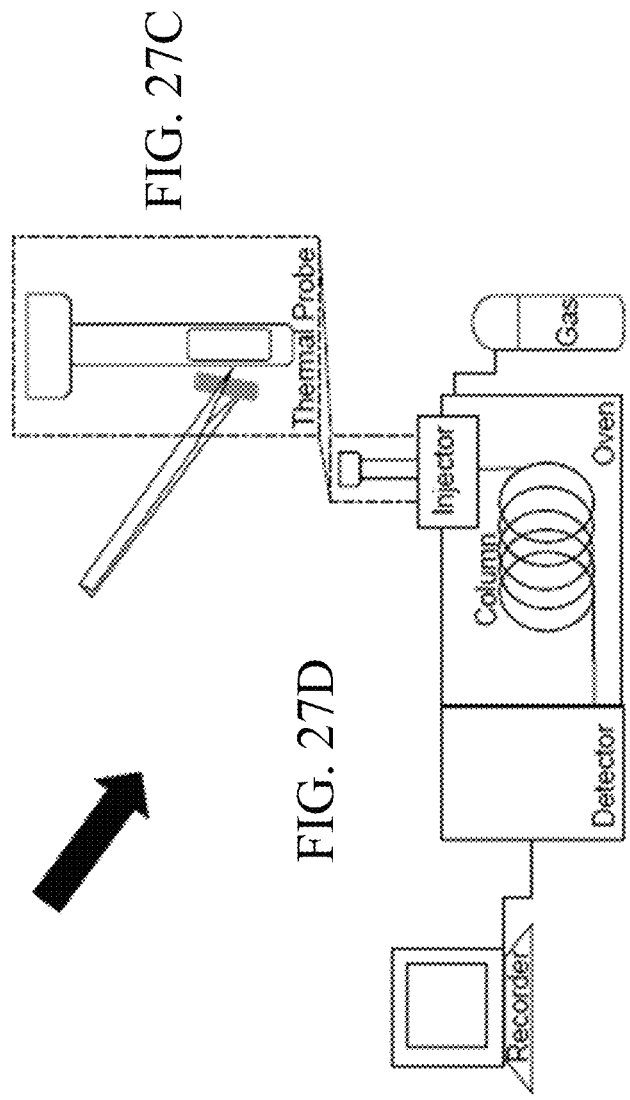
FIG. 27C
FIG. 27D

MATERIALS AND METHODS FOR FIELD TESTING OF CANNABIS SAMPLES

BACKGROUND OF THE INVENTION

The *Cannabis sativa* (Cannabaceae family) plant has been used for medicinal purposes by the Assyrians (3000-2000 BCE), Egyptians (ca. 1500 BCE), Indians, Persians, Greeks, and Romans. Despite its historical use as a "medicine," the plant was eventually banned due to its psychoactive effects. According to data from the United Nations Office on Drugs and Crime (UNODC), the 2017 global seizures of cannabis were 5781 tons. The global number of users is estimated at more than 183 million people (3.8% of the population between 14 and 64 years) in 135 countries and is therefore considered the most widely used illicit drug worldwide.

In the United States and Canada, there has been an increase in the acceptance of the legal, but regulated, use of cannabis for both medicinal and recreational purposes. Although the use and possession of cannabis is illegal under US federal law for any purpose, some state laws conflict with the federal law by legalizing the use of cannabis for medical use (in 33 states) or for recreational use (10 states) with 13 states having decriminalized cannabis use. In addition, the 2018 Farm Bill permits the cultivation and legal trade of Industrial Hemp in the United States.

Hundreds of different natural compounds have been identified in *Cannabis sativa*, in which there are a few cannabinoids responsible for its psychoactive effects. Major compounds found in Cannabis plant, e.g., hemp and marijuana, are tetrahydrocannabinolic acid (THCA) and cannabidiolic acid (CBDA), which decarboxlyate to form $\Delta^9$-tetrahydrocannabinol ($\Delta^9$-THC, with the molecular formula of $C_{21}H_{30}O_2$, and MW of 314 Da) and cannabidiol (CBD, with the molecular formula, $C_{21}H_{30}O_2$ and MW=314 Da), respectively. $\Delta^9$-THC is insoluble in water and soluble in ethanol and petroleum ether and can be found in different parts of the plant at various percentages: (i) 10-12 wt % in flowers, (ii) 1-2 wt % in leaves, (iii) 0.1-0.3 wt % in the stalk, and (iv) <0.03 wt % in the root. An important artefact that forms when $\Delta^9$-THC is heated is cannabinol (CBN, with molecular formula $C_{21}H_{26}O_2$ and MW=310) (FIG. 1).

The new federal Farm Bill, enacted into law in December 2018, makes the cultivation, distribution and sale of hemp legal. The main difference between industrial hemp and the controlled substance, e.g., marijuana, is the concentration of cannabinoids (e.g., THC and CBD) in these plants. Hemp is defined as *Cannabis sativa* and any part or derivative of the plant including seeds that has a tetrahydrocannabinol (THC) concentration below 0.3% (w/w). Cannabis is considered as a controlled substance, e.g., marijuana, when it has a concertation of total THC>0.3%.

Most farmers grow hemp to produce high amounts of CBD for use in food, dietary supplements, cosmetics and other products. Thus, it is important for hemp growers to control the level of THC in their crops so that they have no more than 0.3% at 15 days before harvest, the window of time specified in the USDA rule. Any hemp that contains >0.3% THC is considered to be a controlled substance and needs to be destroyed in strict accordance with applicable laws. In the states where marijuana is legal, it is very preferable for the growers to harvest when the crops have THC that substantially exceeds the 0.3% threshold. Because hemp comprises higher concentrations of CBD than marijuana, while marijuana comprises higher concentrations of THC (>0.3%) than hemp (<0.3%), these cannabinoids are of interest when determining if a suspected plant material is marihuana or industrial hemp.

When Drug Enforcement Administration (DEA) officials (CARFS Industry Advisory Board) were asked to identify a major pain point for DEA in drug analysis, the urgent need to differentiate hemp from marijuana (THC content>0.3%) with a fast and easy to use analytical method in the laboratory and in the field was consistently mentioned.

Current colorimetric tests for qualitative analysis of cannabinoids and derivatives include, for example, the Fast Blue B (FBB) test and the Duquenois-Levine (Du-Le) test. The FBB has been used as a colorimetric reagent. However, it is carcinogenic. In the Du-Le test, vanillin and acetaldehyde are added to a pouch with the plant material. Hydrochloric acid is then added, and if cannabis is present, a purple color forms. Chloroform is then added to extract a deep purple color in the chloroform layer of the reaction for a presumptive positive of cannabis. The Du-Le test, however, does not differentiate between hemp and marijuana as it is a cannabinoid test. The Du-Le test also produces false positives for substances that contain a resorcinol group in them, e.g., for common plants such as spearmint, patchouli, and eucalyptus. $\Delta^9$-THC, CBD, and other cannabinoids contain a resorcinol group and the aliphatic chain group that will extract all the cannabinoids into the chloroform layer of the Du-Le test. Therefore, the Du-Le test is unable to determine the THC:CBD ratio because both form the chromophore in the purple chloroform layer and hence the test is not effective to differentiate between hemp and marijuana.

Thus, there is a pressing need for an analytical test to easily and unambiguously differentiate between the legal hemp plant and the illegal (in most states), marijuana plant, for example, in the field. There is also a need to test commercial plants, in those states where marijuana is legal.

BRIEF SUMMARY OF THE INVENTION

The subject invention provides rapid screening assays and field test kits for differentiating between cannabinoids in a cannabis sample. In preferred embodiments, the assays and kits can be used for differentiating marijuana from other cannabis plants, e.g., hemp. The fast screening field test kit can also be used for confirming the presence of marijuana in a complex sample.

In a preferred embodiment, the methods, and devices can be used for the differentiation between hemp and marijuana for a market where marijuana is illegal and/or regulated. Also, for a market where marijuana is legal, the subject invention provides an inexpensive and easy way to rapidly differentiate between hemp and marijuana plants and/or plant parts or extract.

The method of the subject invention also can be used to test plant material that is suspected of being marijuana in a rapid and accurate manner through a colorimetric test followed by a rapid confirmatory test with, for example, Direct Analysis in Real Time Mass Spectrometry (DART-MS) in a laboratory.

In one embodiment, the subject invention provides a colorimetric test strip comprising a series of reaction wells or pads, and a series of control wells or pads, wherein each reaction well or pad contains a solid substrate preloaded with a chemical reagent, e.g., a colorimetric reagent such as FBBB. In one embodiment, the solid substrate comprising one or more sorbents selected from carbowax, carboxen, divinylbenzene, poly(dimethylsiloxane) (PDMS), sol-gel PDMS, phenyl-modified PDMS (PhPDMS), carbowax/polyethylene glycol (CW/PEG), carbowax/templated resin (CW/TPR), carboxen/polydimethylsiloxane (CAR/PDMS), polyacrylate (PA), divinylbenzene/carboxen/polydimethylsiloxane (DVB/CAR/PDMS), and polydimethylsiloxane/divinylbenzene (PDMS/DVB).

In one embodiment, the solid substrate comprises a capillary microextractor of volatiles (CMV) device. In one embodiment, the CMV comprises a housing having at least two orifices, and a sorbent, wherein the sorbent is porous and/or partitioned, wherein a sample comprising a cannabinoid can flow through the housing orifices and contact the sorbent.

In one embodiment, the chemical reagent reacts with the cannabinoids to specifically differentiate THC from other cannabinoids. Preferably, a specific change of color can be observed by the naked eye from the reaction of the chemical reagent with each cannabinoid in the sample.

In a further embodiment, the housing comprises a material that is thermally stable to at least 300° C. In a specific embodiment, the housing is a glass tube. In some embodiments, the sorbent comprises a film on a support. Preferably, the support comprises a plurality of thermally stable fibers and the film is an amorphous material with a thermal stability of at least 200° C. More preferably, the sorbent comprises a film of a polydimethylsiloxane gel (PDMS gel) on a plurality of glass fibers.

In one embodiment, the colorimetric test strip further comprises a second series of reaction wells, each reaction well containing a solid substrate preloaded with a second chemical reagent, e.g., 4-Aminophenol (4-AP).

In one embodiment, the series of control wells or pads comprises negative control wells or pads, and/or positive control wells or pads, wherein the negative controls do not react with the analytes e.g., cannabinoids, while the positive controls comprise the reactions of the chemical reagents and each analyte (e.g., cannabinoid) of interest at desired concentrations. In a preferred embodiment, the positive control wells display colors generated from the reaction between FBBB and THC, preferably, Δ9-THC, at concentrations less than, equal to, and/or greater than 0.3%.

In one embodiment, the subject invention provides a colorimetric field test kit comprising the colorimetric test strip of the subject invention, at least one color chart, a base, and instructions. In a further embodiment, the colorimetric field test kit may also comprise a solvent selected from, for example, methanol, ethanol, methylene chloride, acetonitrile, water and any combination thereof. In a specific embodiment, the colorimetric test kit may further comprise one or more tools. The measuring tools can be used for, for example, applying the sample to the colorimetric test strip, and/or applying the basic solution to the colorimetric test strip.

In one embodiment, the subject invention provides methods for differentiating marijuana from hemp based on the differences in concentrations of cannabinoids, wherein hemp comprises a concentration of THC≤0.3% while marijuana comprises a concentration of THC>0.3%. Thus, the methods of the subject invention differentiate between marijuana and hemp through, for example, a colorimetric reaction between a colorimetric cannabinoids-binding agent, e.g., the Fast-Blue BB (FBBB) reagent, and THC and/or CBD. For example, a sample comprises >0.3% THC produces a deep red color when react with FBBB while a sample comprising <0.3% THC but predominantly CBD produces an orange color when react with FBBB.

In one embodiment, the method for differentiating marijuana from hemp comprises providing a sample; contacting the sample with the colorimetric test strip of the subject invention; adding a basic solution to the colorimetric test strip; and determining whether the sample comprises marijuana or hemp based on a color generated by a reaction between the sample and the colorimetric reagent in the colorimetric test strip, wherein the red or deep red color is indicative of a marijuana sample with THC exceeding 0.3% threshold, and the orange color is indicative of a hemp sample with THC below 0.3%. In certain embodiments, a color of neither red or deep red, nor orange is generated upon the reaction between the sample and the colorimetric reagent, indicating an inconclusive result. A further confirmation test (e.g., MS) may be needed.

In a preferred embodiment, the sample is an extract that is produced by treatment of the plant, plant part, or plant tissue, and adding a solvent to the treated plant, plant part, or plant tissue.

In one embodiment, the method for differentiating marijuana from hemp further comprises inserting the solid substrate of the colorimetric test strip or the CMV into an injection port of an analytical device configured to separate, detect, and identify one or more analytes in the sample, and determining from the detected and identified one or more analytes the absence or presence of marijuana in the sample.

In one embodiment, the subject invention also provides a method for differentiating THC from CBN and/or CBD comprising providing a sample; contacting the sample with the colorimetric test strip of the subject invention; adding a basic solution to the colorimetric test strip; and determining whether the sample comprises THC or CBD/CBN based on a color generated by a reaction between THC, CBN, or CBD in the sample and the colorimetric reagent in the colorimetric test strip.

Provided herein are analytical measures including sensitivity (LOD), potential interferences (specificity), false positive/false negative rates, uncertainty at different THC/CBD concentration combinations (especially close to the threshold levels) and a standardized color determination using conversion to RGB numerical scores to objectively determine color using color balance-normalized viewing conditions.

BRIEF DESCRIPTION OF THE DRAWINGS

FIGS. 7A-7F show DART(+)MS of the chromophore produced in CMVA support at 400° C. (A, C and E) and 300° C. (B, D and F) between Fast Blue BB reagent and $\Delta^9$-THC, CBD and CBN standards.

FIG. 17 shows the image of 3D structure, and IR Spectra of Intermediate t-bb-2-p (para-coupled intermediate from THC+Fast Blue BB) (Zero point vibrational energy: 506.097 kcal/mol, Total Enthalpy: 535.384 kcal/mol).

FIG. 24 shows the image of 3D structure, and IR Spectra of Intermediate t-bb-4-o (ortho-coupled intermediate from THC+Fast Blue BB) (Zero point vibrational energy: 504.655 kcal/mol, Total Enthalpy: 533.478 kcal/mol).

FIGS. 27A-27D show schematics of the experiment instrument setup. Analytes are absorbed to the CMV device by A) spiking of liquid solution or by B) collection of vapors from the gas generator's outlet. CMV's are placed into a C) thermal desorption probe and undergo D) splitless analysis by gas chromatography-mass spectrometry (GC-MS).

DETAILED DESCRIPTION OF THE INVENTION

Figure 1:
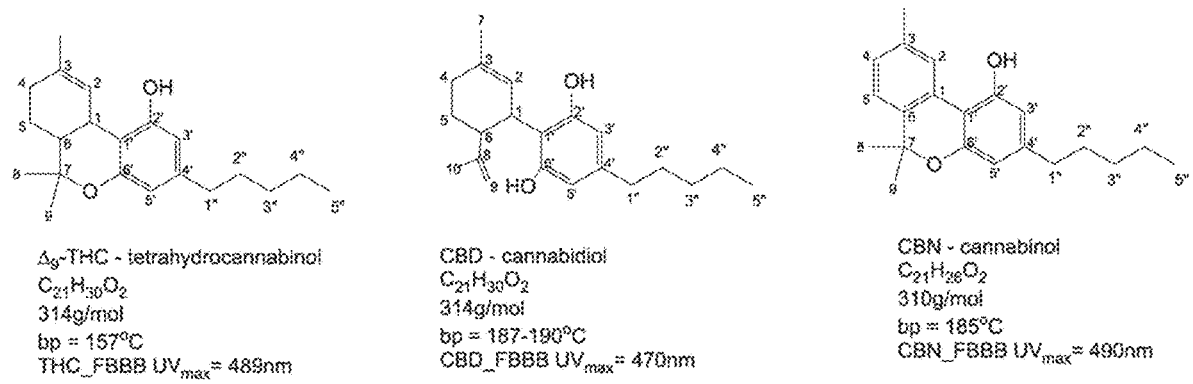
FIG. 1 shows major cannabinoids of interest in the analysis of *Cannabis sativa* L.
Figure 2A:
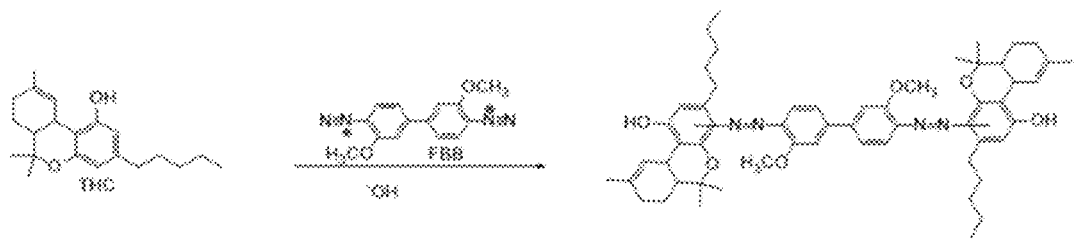
FIGS. 2A-2C show colorimetric compounds formed between $\Delta^9$-THC cannabinoid and specific colorimetric reagents. A) Fast Blue B reagent+THC, B) Fast Blue BB reagent test+THC, and C) Duquenois-Levine test+THC.
Figure 2B:
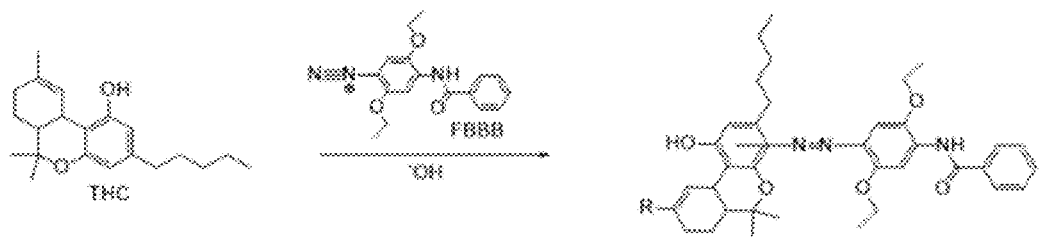
Figure 2C:
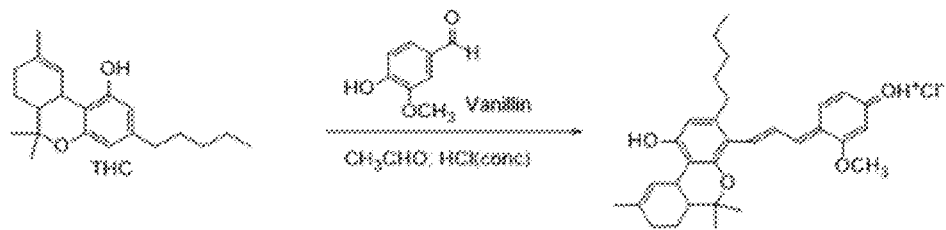

The subject invention provides materials and methods for rapid screening for differentiating between cannabinoids in a cannabis sample. In one embodiment, the subject invention provides screening methods and kits for differentiating marijuana from other cannabis plants, e.g., hemp. The methods and kit can also be used for confirming the presence of marijuana in a seized sample or in a complex cannabis sample.

In one embodiment, the subject invention provides methods and devices that differentiate between cannabinoids in cannabis samples, especially, in the field. In a preferred embodiment, the methods and devices can be used for the differentiation between hemp and marijuana for a market where marijuana is illegal and/or regulated. Also, for a market where marijuana is legal, the subject invention provides an inexpensive and easy way to rapidly differentiate between hemp and marijuana plants and/or extracts from those plants.

In one embodiment, the methods and devices differentiate between cannabinoids in cannabis samples through, for example, a colorimetric reaction between cannabinoids, e.g., THC and CBD, and a cannabinoids-binding agent, e.g., the Fast-Blue BB (FBBB) reagent. Advantageously, the FBBB reaction is more selective with cannabinoids, presents fewer false-positive results than other tests, and forms very stable products, which remain unchanged for more than 7 days.

Cannabinoids include, for example, natural cannabinoids, synthetic cannabinoids, cannabinoid derivative and cannabimimetics. Cannabinoids are chemical compounds that bind to cannabinoid receptors in a subject, preferably, a mammal, more preferably, a human. Cannabinoids are produced in animals, plants, and synthetically. Natural cannabinoids include endocannabinoids that are produced naturally in the body of animals, and phytocannabinoids that are produced naturally in plants such as Cannabis plants. Synthetic cannabinoids are manufactured artificially.

The term "Cannabis plant(s)" includes wild-type *Cannabis sativa* and variants thereof, including Cannabis chemovars, which naturally contain different amounts of the individual cannabinoids and also plants that are the result of genetic crosses, self-crosses, or hybrids thereof.

Phytocannabinoids include, but are not limited to, tetrahydrocannabinol (THC) including delta-8-tetrahydrocannabinol ($\Delta^8$-THC), delta-9-tetrahydrocannabinol ($\Delta^9$-THC), and/or THC metabolites (e.g., THC-COOH), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), and cannabicitran (CBT). Other cannabinoids include, for example, pharmaceutically acceptable salts of cannabinoids.

Field Test Kit

In one embodiment, the field test kit comprises a colorimetric test strip based on materials useful to visually differentiate cannabinoids in cannabis samples. Optionally, such test strip can then be subsequently transported to a laboratory for confirmatory analysis using, for example, GC-MS by direct thermal desorption of the substrate using a probe.

In one embodiment, the subject invention provides a colorimetric test strip comprising a plurality of designated areas for colorimetric reactions, each designated area comprising a supporting material, a solid substrate and one or more chemical reagents. In one embodiment, the supporting material may be, for example, metal, paper, plastic, glass, cloth, and/or polymeric matrix. In one embodiment, the solid substrate comprises one or more sorbents (e.g., PDMS, sol-gel PDMS, and PhPDMS).

In one embodiment, each designated area may be any shape, preferably, circle. Each designated area may have a surface area of at least about 1 mm$^2$, about 2 mm$^2$, about 5 mm$^2$, about 10 mm$^2$, about 15 mm$^2$, about 20 mm$^2$, about 25 mm$^2$, about 30 mm$^2$, about 35 mm$^2$, about 40 mm$^2$, about 45 mm$^2$, about 50 mm$^2$, about 55 mm$^2$, about 60 mm$^2$, about 70 mm$^2$, about 80 mm$^2$, about 90 mm$^2$, or about 100 mm$^2$.

In some embodiments, the designated areas for colorimetric reactions are wells or pads for collecting or absorbing a sample of interest, wherein the wells or pads are preloaded with one or more chemical reagents.

In one embodiment, the subject invention provides a colorimetric test strip comprising a series of reaction wells/pads/sites, and optionally, a series of control wells/pads/sites, wherein each reaction well/pad/site contains a solid substrate preloaded with a chemical reagent that differentiates an analyte of interest from other compounds in a sample. In a preferred embodiment, the chemical reagent is a colorimetric reagent such as FBBB, which can differentiate tetrahydrocannabinol (THC) from other cannabinoids.

In one embodiment, the solid substrate comprises a capillary microextractor of volatiles (CMV) device. In one embodiment, the CMV comprises a housing having at least two orifices, and a sorbent, wherein the sorbent is porous and/or partitioned, wherein a sample comprising a cannabinoid can flow through the housing orifices and contact the sorbent.

In specific embodiments, the solid substrate comprises one or more sorbents selected from carbowax, carboxen, divinylbenzene, poly(dimethylsiloxane) (PDMS), sol-gel PDMS, phenyl-modified PDMS (PhPDMS), carbowax/polyethylene glycol (CW/PEG), carbowax/templated resin (CW/TPR), carboxen/polydimethylsiloxane (CAR/PDMS), polyacrylate (PA), divinylbenzene/carboxen/polydimethylsiloxane (DVB/CAR/PDMS), and polydimethylsiloxane/divinylbenzene (PDMS/DVB).

Figure 29:
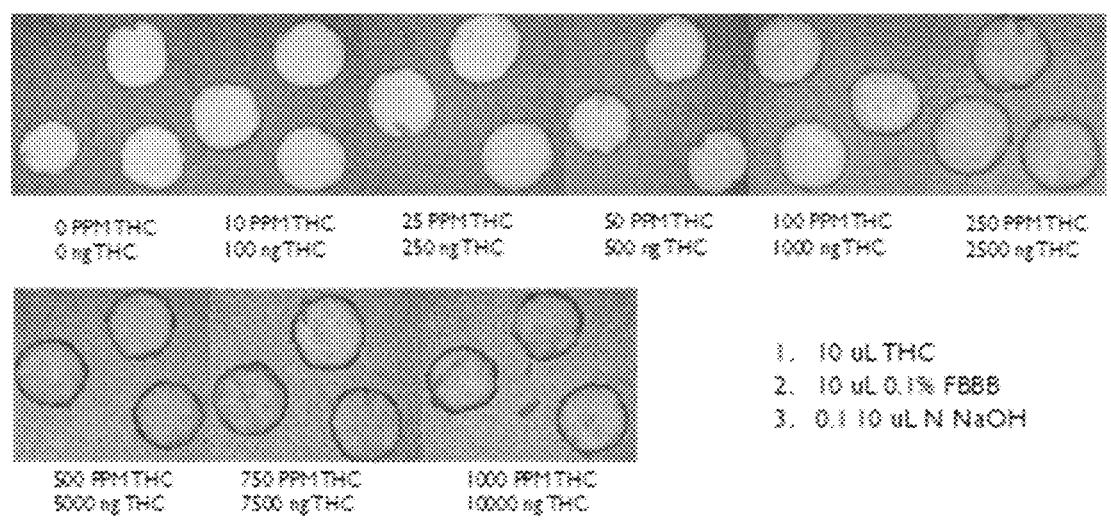
FIG. 29 shows the colors formed between FBBB reagent and total $\Delta^9$-THC at different mass loading equivalents from 0 ng to 5000 ng THC using a 5 mg sample of plant extracted with 1 mL of ethanol and depositing 10 uL of the extract into the well.
Figure 30:
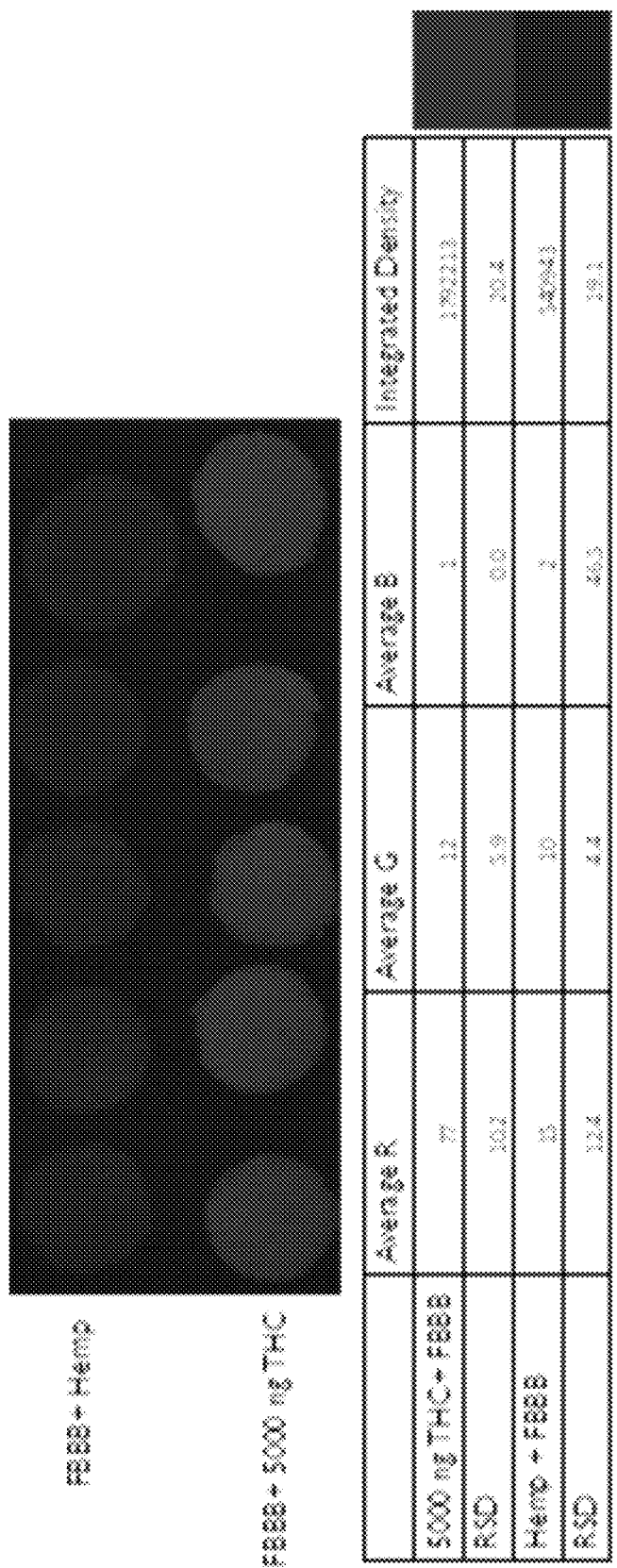
FIG. 30 shows the fluorescence emission associated with the product of the FBBB+$\Delta^9$-THC reaction (red emission with a λmax at 640 nm after 480 nm excitation) in comparison to CBD from a hemp plant extract (no emission) at 5000 ng THC mass loading.

In one embodiment, the chemical reagent reacts with the cannabinoids to specifically differentiate THC from other cannabinoids. Preferably, a specific change of color can be observed by the naked eye from the reaction of the chemical reagent with each cannabinoid in the sample (FIG. 29). In addition a fluorescent source of 480 nm excitation wavelength enables the visualization of the FBBB+THC with a deep red color when no emission is observed for FBBB+CBD (FIG. 30).

Pursuant to the Farm Bill, hemp, also known as fiber-type *cannabis*, has a concentration of total $\Delta 9$-THC$\leq 0.3\%$ (w/w). Hemp is also known to have higher concentrations of CBD than marijuana. In some instances, cannabis that has a THC:CBD ratio below 1 is considered hemp.

Cannabinoids can react with the colorimetric reagent, FBBB. For example, The FBBB+THC and FBBB+CBD reactions produce a color difference between a predominantly $\leq 0.3\%$ THC plant sample that is high in cannabidiol (CBD) (legal in all 50 states) and a predominantly $>0.3\%$ THC plant sample. Marijuana samples exceed the 0.3% THC threshold and form a deep red color when they react with FBBB, while hemp samples contain predominantly CBD (and low THC) and form an orange color when they react with FBBB. The FBBB reagent forms a purple chromophore with CBN when each cannabinoid, e.g., THC, CBD, and CBN, is tested individually. When all three of the cannabinoids are together in solution, the chromophores from CBD and CBN enhance the reddish color formed by THC and FBBB.

The product compounds of the THC and FBBB reaction contain a diazonium group, -+N=N—, where the nitrogen is retained in coupling with the reactive activating group (—OH) of the phenolic group. The product compounds can be characterized through, for example, UV-Vis, TLC, H$^1$NMR, DART-MS/MS, ESI(+)FT-ICR MS, ESI(+)-MS/MS, and molecular modeling calculations. Using UV-Vis the FBBB+$\Delta^9$-THC chromophore can be identified at the 650 nm band, which is responsible for the red color. In basic conditions, THC becomes a phenolate anion that attacks the diazo group to form the chromophore at the para position.

In one embodiment, the colorimetric test strip may be an elongate paper, plastic stick or PDMS slide in which one or more reaction wells/pads/sites and one or more control wells/pads/sites are provided on one side of the strip and one end of the strip is used as a grip portion. The side provided with the reaction wells/pads/sites is the front/up side.

In one embodiment, the colorimetric test strip comprises one or more small reaction wells/pads/sites that comprise sorbent-coated glass microfiber substrate materials. In one embodiment, the coating of the glass microfibers can be used as extraction substrates that retain the compounds of interest.

The sorbent may be, for example, carbowax, carboxen, divinylbenzene, poly(dimethylsiloxane) (PDMS), sol-gel PDMS, phenyl-modified PDMS (PhPDMS), carbowax/polyethylene glycol (CW/PEG), carbowax/templated resin (CW/TPR), carboxen/polydimethylsiloxane (CAR/PDMS), polyacrylate (PA), divinylbenzene/carboxen/polydimethylsiloxane (DVB/CAR/PDMS), or polydimethylsiloxane/divinylbenzene (PDMS/DVB). Preferred sorbents are PDMS, sol-gel PDMS, and/or PhPDMS.

In one embodiment, the wells of the colorimetric test strip are deep enough to allow the reagents to collect and react. The well may hold as low as, for example, 2 μL, 5 μL, 10 μL, 15 μL, 20 μL, 25 μL, 50 μL, 100 μL, 150 μL, or 200 μL.

In one embodiment, the reaction well has a diameter from about 1 mm to about 20 mm, from about 1 mm to about 15 mm, from about 2 mm to about 12 mm, from about 2 mm to about 10 mm, from about 2 mm to about 9 mm, from about 2 mm to about 8 mm, from about 2 mm to about 7 mm, from about 2 mm to about 6 mm, from about 3 mm to about 6 mm, or from about 3 mm to about 5 mm. In specific embodiments, the reaction well has a diameter of 3, 4, 5, 6, 7, 8, 9, 10, 11, 12, 13, 14, 15, 16, 17, 18, 19, or 20 mm.

In one embodiment, the colorimetric test strip may be cut off from a testing sheet having a length of 1 inch to 10 inches and a width of 1 inch to 10 inches. In certain embodiments, the colorimetric test strip may have a length of, for example, 10 mm to 10 inches, 10 mm to 9 inches, 10 mm to 8 inches, 20 mm to 7 inches, 2 mm to 6 inches, 1 inch to 5 inches, 1 inch to 4.5 inches, 1.5 inch to 4 inches, or 2 inch to 3.5 inches. In certain embodiments, the colorimetric test strip may have a width of, for example, 2 mm to 5 inches, 5 mm to 4.5 inches, 10 mm to 4 inches, 15 mm to 3.5 inches, 20 mm to 3 inches, or 1 inch to 2.5 inches.

In one embodiment, the colorimetric test strip comprises 1 to 20 reaction wells, preferably, 1 to 18, 1 to 16, 1 to 15, 1 to 14, 1 to 12, or 1 to 10 reaction wells, more preferably, 2 to 16, 2 to 15, 2 to 12, 2 to 10, or 2 to 8 reaction wells.

In one embodiment, the colorimetric test strip comprises one or more small reaction wells comprising a sorbent-coated glass microfiber substrate loaded with a chemical reagent, for example, FBB, FBBB and/or 4-AP. In one embodiment, the colorimetric test strip also comprises one or more control wells comprising a sorbent-coated glass microfiber substrate that does not contain any reaction reagents. Such control wells may be used as negative controls.

In a specific embodiment, the colorimetric test strip comprises a plurality of designated areas of one or more sorbents preloaded with a colorimetric reagent. Preferably, the sorbent comprises PDMS, sol-gel PDMS or PhPDMS, and the colorimetric reagent is FBBB.

In one embodiment, the colorimetric test strip further comprises one or more standard wells containing a known amount of internal standard. Such standard wells may be used as positive controls. In a preferred embodiment, the positive control wells display colors generated from the reaction between FBBB and THC, preferably, Δ9-THC, at concentrations less than, equal to, and/or greater than 0.3%. In some embodiment, the positive control further comprises wells that display colors generated from the reaction between FBBB and CBD, the reaction between FBBB and CBN, the reaction between FBBB and the mixture of CBD and CBN, and/or the reaction between FBBB and the mixture of THC, CBD and CBN.

In certain embodiments, the positive control wells comprise a range of concentrations of cannabinoids, wherein the range of concentrations includes any three or more of, for example, 0.001%, 0.005%, 0.01%, 0.05%, 0.1%, 0.2%, 0.3%, 0.5%, 1%, 2%, 3%, 4%, 5%, 7.5%, 10%, 12.5%, 15%, 20%, 25%, 30%, 35%, 40%, 45%, 50%, 60%, 70%, 80/o, and 90%.

In one embodiment, the colorimetric test strip comprises one or more capillary microextraction of volatiles (CMV) devices/substrates containing a pre-loaded reaction reagent, for example, FBBB or 4-AP. The CMV is based on an adsorption (or absorption) phase coated substrate packed inside a double open-ended glass capillary (e.g., 2 cm×2 mm). These dimensions are designed to fit into a commercially available thermal separation probe (TSP) that can be placed directly into a GC injection port for thermal desorption.

In one embodiment, the CMV comprises a tube or other housing that contains an absorbent, with a high surface area and/or high diffusivity. The material of the tube or other housing is generally, but not necessarily, a non-absorbing material. For example, the tube can be glass, ceramic, metal, or thermally-stable polymer, for example, a polyimide, such as Kapton, or a polybenzimidazole.

The high surface area absorbent may be a thin film on a solid support. The high surface area absorbent preferably comprises a non-flowing material or is sufficiently viscous to be essentially non-flowing. The absorbent can be amorphous and thermally-stable to temperatures in excess of about 200° C. or more, for example, stable at 250° C. or more.

Because of the high surface area and/or inherent ability of the sorbent to permit rapid flow and/or diffusion onto and/or into the sorbent, one or more chemicals contained in a sample contacting the sorbent can be rapidly sampled. In specific embodiments, the CMV comprises a small capillary tube containing glass fiber filter strips coated with one or more sorbents, e.g., PhPDMS and/or PDMS.

Advantageously, the CMV is able to withstand high temperatures (e.g., about 300° C. or more) without degradation making it amenable for use in DART-MS analysis. This allows for the visualization of the reaction chromophore, e.g., the FBBB and THC chromophore, followed by its confirmation through DART-MS or other MS analysis. The tests according to the subject invention reduce the analysis time required to confirm whether a plant is hemp or marijuana.

The non-polar nature of the CMV sorbent does not permit the reagents of the FBBB and THC reaction to spread, thereby facilitating a more intense red color to be produced in the presence in a plant with a high concentration of THC or an orange color in the case of a high concentration of CBD. This allows for the screening of marijuana from plant material.

In a specific embodiment, a CMV device or a strip/circle of the PDMS/Phenyl Modified PDMS (PhPDMS) sorbent is used as the substrate for the colorimetric reaction between FBBB and Delta-9-Tetrahydrocannabinol from marijuana plants and/or marijuana plant extracts to differentiate between marijuana (high THC) and hemp (low THC and, generally, high CBD).

In a specific embodiment, the colorimetric test strip comprises a series of wells with only the FBBB reagent pre-loaded in the CMV or substrates. In a specific embodiment, the colorimetric test strip also comprises a second series of wells with only the 4-AP reagent pre-loaded in the CMV or substrates.

In one embodiment, there may be additional sorbent coatings to the first sorbent coating (e.g., PDMS) of glass microfibers. The additional sorbent coatings to, for example, PDMS improve the sampling and preconcentration of aromatic compounds.

In one embodiment, the colorimetric test strip may have numbers labeling each reaction well, control well, or standard well. The colorimetric test strip may also have a logo mark, a bar code, or reaction reagent label on the front/up or back/down side of the strip.

In one embodiment, the colorimetric test strip of the subject invention can selectively detect THC as low as, for example, 50 ng, 100 ng, 125 ng, 150 ng, 200 ng, 250 ng, 300 ng, 350 ng, 400 ng, 450 ng, or 500 ng. Preferably, the colorimetric test strip of the subject invention can selectively detect THC as low as 50 ng.

In one embodiment, the colors can be developed in the field test strip or CMV within, for example, 5 seconds, 10 seconds, 15 seconds, 20 seconds, 30 seconds, 1 minute, 1.5 minutes, 2 minutes, or 5 minutes.

In one embodiment, the field test kit also comprises a base, for example, NaOH, KOH, and/or $NH_4OH$.

In one embodiment, the field test kit also comprises a color chart that displays the expected colors based on the presence or absence of the compounds of interest. In a specific embodiment, the color chart displays the expected colors generated from the reaction between the chemical reagent and each cannabinoid of interest, including CBD and THC, preferably, $\Delta 9$-THC. In a preferred embodiment, the color chart displays the expected colors generated from the reaction between FBBB and THC, preferably, $\Delta 9$-THC, at concentrations less than, equal to, and/or greater than 0.3%.

In one embodiment, the field test kit may further comprise a second color chart that displays the range of concentrations expected according to color intensities of each compound of interest. The range of concentrations may include any three or more of for example, 0.001%, 0.005%, 0.01%, 0.05%, 0.1%, 0.2%, 0.3%, 0.5%, 1%, 2%, 3%, 4%, 5%, 7.5%, 10%, 12.5%, 15%, 20%, 25%, 30%, 35%, 40%, 45%, 50%, 60%, 70%, 80%, and 90%.

In one embodiment, the field test kit also comprises one or more solvents for preparing a test sample to be added to the colorimetric test strip. In specific embodiments, the solvent may be, for example, methanol, ethanol, petroleum ether, methylene chloride, acetonitrile, water, or any combination thereof. Preferably, the solvent is methylene chloride.

In one embodiment, the field test kit further comprises one or more tools, e.g., measuring tools, for preparing a test sample, and/or for adding the test sample into the reaction wells of the test strip. Such tools may include, but are not limited to, pipettes, syringes, and spoons.

In one embodiment, the field test kit also comprises instructions providing information regarding each component of the field test kit, including, for example, reagents, test strips, CMVs, solvents, and/or bases. The instruction also provides information on how to prepare a test sample, and/or perform the tests using the field test kit.

In one embodiment, the test strip of the subject invention has a long shelf life. The preloaded reagents are stable over a long time period, such as, for example, up to 6 months, 12 months, 18 months, 24 months, 30 months, 36 months, or 4 years.

Method of Use

In one embodiment, the subject invention provides methods for differentiating marijuana from other cannabis plants, e.g., hemp, by using the field test kit of the subject invention.

In one embodiment, the method comprises providing a sample comprising plant materials, obtaining a plant extract by mixing the sample with an extraction solvent, contacting the plant extract with a colorimetric test strip of the subject invention by adding the plant extract in one or more designated areas, e.g., one or more reaction wells/pads/sites, and/or control wells/pads/sites, of the colorimetric test strip, adding a basic solution to the one or more designated areas, e.g., reaction wells/pads/sites, and/or control wells/pads/sites, and determining whether the sample comprises marijuana or hemp based on a color generated by a reaction between the sample and the colorimetric reagent in the colorimetric test strip, wherein a red or deep red color is indicative of a marijuana sample with THC exceeding 0.3% threshold, and an orange color is indicative of a hemp sample with THC below 0.3%.

In one embodiment, the determination of the marijuana sample or hemp sample may involve comparing the color of the reaction wells/pads/sites with a color chart. Alternatively, the color of the reaction wells/pads/sites can be compared with the color of positive controls.

In a specific embodiment, the method for differentiating marijuana from other cannabis plants, e.g., hemp, comprises providing a sample comprising plant materials, obtaining a plant extract by mixing the sample with an extraction solvent, contacting the plant extract with a colorimetric test strip of the subject invention by adding the plant extract to the designated areas of sorbents, e.g., PDMS or PhPDMS, of the colorimetric test strip, adding a basic solution to the designated areas of sorbents, and determining whether the sample comprises marijuana or hemp based on a color generated by a reaction between the sample and the colorimetric reagent in the colorimetric test strip, wherein a red or deep red color is indicative of a marijuana sample with THC exceeding a threshold (e.g., 0.3%), and an orange color is indicative of a hemp sample with THC at or below the threshold.

In some embodiments, the method of the subject invention comprises providing a sample comprising plant materials, obtaining a plant extract by mixing the sample with an extraction solvent, contacting the plant extract with one or more CMVs of the subject invention, wherein at least one component of the plant extract is absorbed by one or more CMVs, adding a basic solution to the one or more CMVs, and determining whether the sample comprises marijuana or hemp based on the color of the CMVs, wherein a red or deep red color is indicative of a marijuana sample with THC exceeding 0.3% threshold, and an orange color is indicative of a hemp sample with THC below 0.3%.

In one embodiment, the determination of the marijuana sample or hemp sample may involve comparing the color of CMVs with a color chart. Alternatively, the color of the CMVs can be compared with the color of positive controls.

In one embodiment, the method for differentiating marijuana from other *cannabis* plants, e.g., hemp, further comprises desorbing the at least one component of the plant extract from the solid substrate of the test strip, e.g., the CMVs/sorbent into an injection port of an analytical device configured to separate, detect, and identify the at least one component of the plant extract; and determining from the detected and identified at least one component of the plant extract whether the sample comprises marijuana or hemp.

In one embodiment, the subject invention provides methods for detecting marijuana in a sample, or for determining a sample as being marijuana, by using the field test kit of the subject invention. The method comprises providing a sample comprising plant material, obtaining a plant extract by mixing the sample with an extraction solvent, contacting the plant extract with a colorimetric test strip of the subject invention by adding the plant extract in one or more designated areas, e.g., one or more reaction wells/pads/sites, and/or control wells/pads/sites, of the colorimetric test strip, adding a basic solution to one or more designated areas, e.g., the reaction wells/pads/sites and/or control wells/pads/sites, and detecting the absence or presence of marijuana in the sample based on the color of one or more designated areas, e.g., the reaction wells/pads/sites.

In a specific embodiment, the method for detecting marijuana in a sample comprises providing a sample comprising plant materials, obtaining a plant extract by mixing the sample with an extraction solvent, contacting the plant extract with a colorimetric test strip of the subject invention by adding the plant extract to the designated areas of sorbent, e.g., PDMS or PhPDMS, adding a basic solution to the designated areas of sorbent, and detecting the absence or presence of marijuana in the sample based on the designated areas of sorbent.

In some embodiments, the method for detecting marijuana in a sample, or for determining a sample as being marijuana comprises providing a sample comprising plant materials, obtaining a plant extract by mixing the sample with an extraction solvent, contacting the plant extract with one or more CMVs of the subject invention, wherein at least one component of the plant extract is absorbed by one or more CMVs, adding a basic solution to the one or more CMVs, and determining the absence or presence of marijuana in the sample based on the color of the CMVs.

In one embodiment, the method for detecting marijuana in a sample further comprises desorbing the at least one component of the plant extract from the CMV into an injection port of an analytical device configured to separate, detect, and identify the at least one component of the plant extract; and determining from the detected and identified at least one component of the plant extract the absence or presence of marijuana in the sample.

In one embodiment, the subject invention provides methods for detecting hemp in a sample, or for determining a sample as being hemp by using the field test kit of the subject invention followed by separation, detection, and identification of the components of hemp via an analytical device. In one embodiment, the analytical device comprises a gas chromatograph coupled to a mass spectrometer (GC/MS), DART(+)MS and/or DART(+)MS/MS.

In preferred embodiments, the CMV of the subject invention comprises a glass capillary tube containing a fibrous glass material, wherein the fibrous glass material is coated with one or more sorbent, such as PDMS, sol-gel PDMS, and/or PhPDMS.

In one embodiment, the extraction solvent may be, for example, methanol, ethanol, petroleum ether, methylene chloride, acetonitrile, water and any combination thereof. Preferably, the solvent is methylene chloride.

In one embodiment, the subject invention provides methods for differentiating THC, such as $\Delta^9$-THC, from other cannabinoids such as CBD, and/or CBN, by using the colorimetric test strip of the subject invention. The method comprises providing a sample, contacting the sample with a colorimetric test strip of the subject invention by adding the sample in one or more designated areas, e.g., one or more reaction wells and/or control wells, of the colorimetric test strip, adding a basic solution to one or more designated areas, e.g., the reaction wells and/or control wells, and determining whether the sample comprises THC, CBD, and/or CBN based on the colors of one or more designated areas, e.g., the reaction wells.

In one embodiment, the method may also comprise providing a sample, contacting the sample with one or more CMVs of the subject invention by adding the sample onto the one or more CMVs, adding a basic solution to the one or more CMVs, and determining whether the sample comprises THC, CBD, and/or CBN based on the colors of the CMVs.

In one embodiment, the subject invention provides methods for detecting a cannabinoid, such as THC, e.g., $\Delta^9$-THC, in a sample, by using the field test kit of the subject invention. The method comprises providing a sample, contacting the sample with a colorimetric test strip of the subject invention by adding the sample in one or more designated areas, e.g., one or more reaction wells and/or control wells, of the colorimetric test strip, adding a basic solution to one or more designated areas, e.g., the reaction wells and/or control wells, and detecting the absence or presence of THC in the sample based on the colors of one or more designated areas, e.g., the reaction wells.

In some embodiments, the method for detecting a cannabinoid, such as THC, e.g., $\Delta^9$-THC, in a sample, may comprise contacting the sample with one or more CMVs of the subject invention, wherein if present, THC in the sample is absorbed by one or more CMVs, adding a basic solution to the one or more CMVs, and determining the absence or presence of THC in the sample based on the colors of the CMVs e.g., by comparing the color of the one or more CMVs with a color chart. In one embodiment, the subject invention provides methods for detecting CBN and/or CBD in a sample, by using the field test kit of the subject invention.

In one embodiment, the method for detecting a cannabinoid such as THC, CBD, or CBN in a sample further comprises desorbing THC, CBD, or CBN from the solid substrate of the colorimetric test strip, e.g., the CMV/sorbent, into an injection port of an analytical device configured to separate, detect, and identify THC, CBD, or CBN in the presence of the sample.

In one embodiment, the sample is a seized sample, e.g., seized drug sample, for instance, a plant material sample, or a street drug sample seized by law enforcement or school or government officials.

Preferably, the sample is a plant, plant part, or plant tissue. Plant part includes, for example, flower, stalk, seed, bud, leave, and root. The obtained plant or plant tissue may be directly used, or may be also subjected to pretreatment (washing, cutting, or the like).

In one embodiment, the sample may also be a fluid from a subject, preferably, a mammal, more preferably, a human. The fluid may be, for example, sativa, blood, serum, plasma, urine, and sweat.

In one embodiment, the test using the colorimetric test strip or CMV of the subject invention does not require a large volume of samples. In fact, the test using the colorimetric test strip or CMV of the subject invention reduces the volume of reagent required. For example, the volume of samples can be from about 2 µL to about 1000 µL, 2 µL to about 900 µL, 2 µL to about 800 µL, 2 µL to about 700 µL, 2 µL to about 600 µL, 2 µL to about 500 µL, 2 µL to about 400 µL, 2 µL to about 300 µL, 2 µL to about 200 µL, from about 2 µL to about 150 µL, from about 2 µL to about 120 µL, from about 2 µL to about 100 µL, from about 2 µL to about 90 µL, from about 2 µL to about 80 µL, from about 2 µL to about 70 µL, from about 2 µL to about 60 µL, from about 2 µL to about 50 µL, from about 2 µL to about µL, from about 2 µL to about 30 µL, from about 2 µL to about 20 µL, from about 5 µL to about 20 µL, or from about 5 µL to about 15 µL. Preferably, the volume of samples can be, for example, 2 µL, 5 µL, 10 µL, 15 µL, 20 µL, 25 µL, 50 µL, 100 µL, 150 µL, or 200 µL.

In specific embodiment, with the field test kit of the subject invention, the user can conduct a ~1 mL solvent extraction of a small amount 10 mg of the plant material. A small amount (~10 uL) of the solvent extract can then be dropped into each well and the color reaction is observed after adding a base. For example, a red color in the FBBB well and blue color in the 4-AP well would indicate marijuana while an orange color and pink color will indicate that the plant is hemp.

In one embodiment, the test strip of the subject invention can be used for determining/estimating the concentration of the compound of interest (e.g., THC) in each well/sample based on the color intensity. The color intensity can be compared to a color chart that displays the concentrations according to color intensity.

For example, a standard curve may be made by evaluate the compound of interest, e.g., THC, 4-AP, and CBD, at any three or more concentrations selected from, for example, 0.001%, 0.005%, 0.01%, 0.05%, 0.1%, 0.2%, 0.3%, 0.5%, 1%, 2%, 3%, 4%, 5%, 7.5%, 10%, 12.5%, 15%, 20%, 25%, 30%, 35%, 40%, 45%, 50%, 60%, 70%, 80%, and 90%. The colors and their intensity can be observed at each concentration. A second standard curve may also be made by evaluate the compound of interest, e.g., THC, in the presence of one or more interfering compounds and/or other cannabinoids, e.g., CBD, at, for example, any three or more concentrations selected from 0.001%, 0.005%, 0.01%, 0.05%, 0.1%, 0.2%, 0.3%, 0.5%, 1%, 2%, 3%, 4%, 5%, 7.5%, 10%, 12.5%, 15%, 20%, 25%, 30%, 35%, 40%, 45%, 50%, 60%, 70%, 80%, and 90%, providing insight as to threshold of e.g., THC/CBD ratio.

In one embodiment, the methods according to the subject invention may further comprise a step of determining/measuring the concentrations of each compound of interest, e.g., THC, CBD, and CBN, in the test sample.

In one embodiment, the test strip of the subject invention can be used for determining the ratio of THC and CBD in a sample.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Materials and Methods
Reagents and Standards

Standards of methanolic solutions (1 mg mL$^{-1}$) of $\Delta^9$-tetrahydrocannabinol ($\Delta^9$-THC), ethanolic solutions (25 mg mL$^{-1}$) of $\Delta^9$-THC, 11-nor-9-carboxy-$\Delta^9$-THC ($\Delta^9$-THC-COOH), 11-Hydroxy-$\Delta^9$-THC ($\Delta^9$-THC-OH), CBN, CBD and Fast Blue BB Salt were obtained from Sigma Aldrich (USA). Solutions of 0.1% of FBBB and 0.1% NaOH in methanol were prepared as well as standard solutions of cannabinoids in 1000; 100; 50, 25, 10 and 5 ppm. Commercial teas in tea bags were bought with the aim to detect possible false-positive results. We acquired teas that had one or more plant species as the active ingredients. These plants were chosen since they are most commonly found in USA commerce and have phenolic compounds and terpenes derivatives. Table 1 shows the brand and their plants per bag. Sour Space Scan, Kush Outdoor Connoisseur, and Melon-Berry Hemp strains were purchased from Blue Ridge Hemp Co. Due to the Hop plant being closely related to Cannabis Hops Pellets and Hop Leaves were purchased for false positive tests. Azacca and Apollo hops pellets were bought from commercial retailers. Citra Whole Leaf Hops were purchased from Yamacha Chief Hop Union.

TABLE 1

Chemical shifts ($\delta$) in ppm of $^1$H NMR data corresponding to chromophore $\Delta^9$-THC plus FBBB and FBBB reagents according to literature.

| Position | $^1$H NMR of THC plus FBBB | $^1$H NMR of FBBB | |
|---|---|---|---|
| 1 | | | |
| 2 | 4.11 (q, | 3.23 (q, | FBBB |
| —CH$_2$— from 2-Ethoxy | J = 6.8 Hz, 2H) | J = 6.8 Hz, 2H) | molecular portion |
| 3 | 7.06 | 6.58 | |
| 4 | | | |
| 5 | 3.97 (q, | 3.02 (q, | |
| —CH$_2$— from 5-Ethoxy | J = 7.0 Hz; 2H) | J = 7.0 Hz, 2H) | |
| CH$_3$ from 2 and 5 ethoxy | 1.35 (td, J = 7.0, 4.8 Hz, 6H) | 0.27 (td, J = 7.0, 4.3 Hz, 6H) | |
| 6 | 7.94 | 7.41 | |
| ortho-benzamide group | 7.78-7.73 (m, 2H) | 6.69-6.65 (m, 2H) | |
| meta-benzamide group | 7,40 (dd, J = 8.1, 6.7 Hz, 2H) | 6.33-6.27 (m, 2H) | |
| para-benzamide group | 7.47 (m, 1H) | 6.43-6,37 (m, 1H) | |

TABLE 1-continued

Chemical shifts (δ) in ppm of $^1$H NMR data corresponding to chromophore $\Delta^9$-THC plus FBBB and FBBB reagents according to literature.

| Position | $^1$H NMR of THC plus FBBB | $^1$H NMR of FBBB |
|---|---|---|
| 1 | 2.97 (d, J = 108 Hz, 1H) | THC molecular portion |
| 2 | 6.07 | |
| 3 | 1.58 (s, 3H) | |
| 3-Me | | |
| 4 | 2.07 (m, 2H) | |
| 5 | 1.33 | |
| 6 | 1.85 (d, J = 12.5 Hz, 1H) | |
| 3 | | |
| 7 | | |
| 8 | 1.57 (s) | |
| 9 | 1.14 (s) | |
| 1' | | |
| 2' | | |
| 3' | 6.02 | |
| 4' | | |
| 5' | | |
| 1" | 2.55 (dd, J = 8.6, 4.9 Hz, 2H) | |
| 2" | 1.52 (m) | |
| 3" | 1.28 (m, 2H) | |
| 4" | 1.28 (m, 2H) | |
| 5" | 0.80 (m) | |

False Positive Tests with Fast Blue BB

Three different extracts for the tea bags were prepared using 20 mL of water, methanol and methylene chloride and leaving the bags in the solvent for 24 hrs. To conserve samples and reagents, Hemp and Hop extracts were prepared by weighing out 100 mg of each sample and extracting with 2 mL of solvents. After the preparation step, 10 µL of each extract was placed in a filter paper and 10 µL of FBBB 0.1% (wt %) was posteriously added, followed by 10 µL of NaOH 0.1% (wt %). The positive result was confirmed by the evolution of a reddish color on the filter paper.

Reaction Between Δ9-THC and FBBB and Isolation of the Product

The reaction of $\Delta^9$-THC with FBBB salt occurred by the addition of 10 mg of FBBB in ethanolic solution equivalent a 10 mg $\Delta^9$-THC, with 10 mg of NaOH in a glass vial of 20 mL. A TLC was employed in the evaluation of the reaction and isolation of the products. For this process, the stationary phase was silica in a plastic support and methylene chloride as the mobile phase. The column chromatography allowed the purification of the reaction products. Alumina was used as the stationary phase and methylene chloride (500 mL) for the elution of the samples. Forty-six fractions, 3 mL each, were collected, where the pure fractions (between 35 and 38) produced, as well as, the FBBB reagent was analyzed by $^1$H NMR, DART(+)MS and DART(+)MS/MS.

Evaluation of Support of DART-MS

A support was used to detect the cannabinoids using DART-MS analysis. The end of filter paper strips (Whatman 42) and strips of glass filter coated with sol-gel were spiked with 10 µL of solutions of the standard followed by 10 µL each of FBBB and NaOH 10% in methanol. The glass filter coated strips with sol-gel was prepared with PhPDMS and PDMS with an adsorption phase that composes the devices Capillary Microextraction of Volatiles (CMV), here denoted as CMV-A and CMV-B, respectively. The coated glass filters were cut into strips of 2 cm length and ~2 mm width, with 7 strips packed inside glass capillary tubes. The CMV-A was prepared by adding 3.2 g vt-PDMS dissolved in 3.5 mL methylene chloride in a 50 mL polypropylene tube followed with 2.25 mL PhTMOS, 0.83 mL PMHS and 1.37 mL TFA (5% water v/v) with vortex agitations after each addition. The final solution was sonicated for 10 min and allowed to sit for an additional 20 min at ambient conditions. The CMV-B was prepared with 3.2 g vt-PDMS dissolved in 3.9 mL methylene chloride, followed by volumes of 1.71 mL MTMOS, 0.83 mL PMHS and 1.37 mL TFA (5% water v/v) consecutively and accompanied by vortex agitations. The final solution was allowed to stay at ambient conditions for 30 min, with no sonication.

The glass filters coating was prepared by pipetting 2.1 mL of the PhPDMS or PDMS sol-gel solutions over the activated filters which were placed on an interface glass slide held by vacuum on the chuck of a spin coater and spun immediately at 1000 rpm for 1 min. The coated filters were placed inside a desiccator maintained under vacuum for 1 h and then rinsed with methylene chloride for 5 min. Finally, the washed coated filters were placed in the oven for gradual controlled heating: starting at 40° C. for 4 h, 120° C. for 1 h, 240 C for 1 h and 300° C. for 3 h followed by cooling at a slow rate (8 C min$^{-1}$) to ambient temperature. The CMV-A and CMV-B devices were used for the evaluation of the reaction between $\Delta^9$-THC and FBBB.

GC-MS Analysis

An Agilent 7890A gas chromatograph connected to a 5975C inert XL MSD with a triple axis detector (Agilent Technologies, Santa Clara, Calif.) was used for the direct thermal desorption of the CMV samples. The devices were thermally desorbed by placing them on an Agilent TSP installed on the split/splitless GC injection port. A DB-5 ms Ultra Inert column (28.65 µm×0.25 µm×0.25 µm, Agilent Technologies, Santa Clara, Calif.) was used for chromatographic separation with a helium flow rate of 1.2 mL min$^{-1}$. The injector was fitted with a Sky® 4 mm ID single taper inlet liner (Restek, Bellefonte, Pa.) and set at 250° C. in a split mode at 5:1 ratio. The temperature of the GC oven was programmed at 40° C. with 3 min hold, followed by an increase to 270° C. at 20° C. min$^{-1}$ with a 3 min hold (19.5 min run time). The temperatures of the EI source, the transfer line to the mass spectrometer, and the quadrupoles were set to 230° C., 280° C., and 150° C., respectively.

DART-MS Analysis

The DART-MS analysis was conducted using a 6530 Q-TOF MS (Agilent, Santa Clara, Calif.) coupled to a DART SVP (Ion Sense, Saugus, Mass.) ambient ionization source. DART ion source control was achieved through the DART SVP software (v 3.0.x). Mass spectra and Q-TOF data acquisition were achieved using Mass Hunter Workstation Software LC/MS Data Acquisition. Mass spectra interpretation was performed using a MassHunter Workstation Software qualitative Analysis. The analysis were conducted in positive-ion ionization mode, DART(+), with a temperature heating of helium gas at 300 and 400° C. The Q-TOF was maintained at a heated gas (helium) of 350° C., drying gas flow at 3 L min$^{-1}$, fragmentor voltage of 175 V, skimmer voltage 65 V, and a mass range of 40-800 amu. Collision-induced dissociation (CID) experiments were also performed for some targeted signals (m/z 311, 315, 622 and 626), varying the collision energy from 0.0; 30.0; 60.0 to 120 V. The full scan mode was used for acquiring data. The samples consisted of placing 10 µL of the different concentration of cannabinoids standards ($\Delta^9$-THC, CBD, and CBN) in a support, adding 10 µL of FBBB, followed by 10 µL of NaOH (in proportion of 1:1:1) until the development of a reddish color. The solutions of the samples were placed on the support and passed through the DART source ion stream.

Nuclear Magnetic Resonance (NMR)

$^1$H NMR 1D and 2D analyzes were recorded in a Bruker Spectrospin 400 ultra-shield 400 MHz with internal reference TMS. Two pure fractions were acquired from the column chromatography and were solubilized in methanol and chloroform deuterated solvents. A solution of 10 mg mL$^{-1}$ of the FBBB reagent was made and solubilized in methanol. All of the NMR spectra data were analyzed by MestReNova version 6.0.2-5475.

Theoretical Methods

In order to study the formation of products that give a positive colorimetric change between the reactions of $\Delta^9$-THC with FBBB, ab initio calculations were performed at the B3LYP/3-21g level of theory. This density functional theory (DFT) with the B3LYP functional was chosen because it has been widely used and accepted in the theoretical chemistry community, and the 3-21g basis set was chosen as a compromise between computational cost and structural accuracy. The expected products that yield a color change consist of 93 atoms, of which 46 are heavy atoms (non-hydrogens) and the reaction mechanism spans the $C_{38}H_{48}O_5N_3$ PES. The optimized structures were used in calculations of the electronic energy, vibrational frequencies, IR spectra, and zero-point energies are shown in FIGS. 12-25. The geometry optimizations and vibrational frequency analysis were done using the QChem 5.1 software, while relaxed PES scans were done using Gaussian16.

Example 1—the Test Strip

Figure 3:
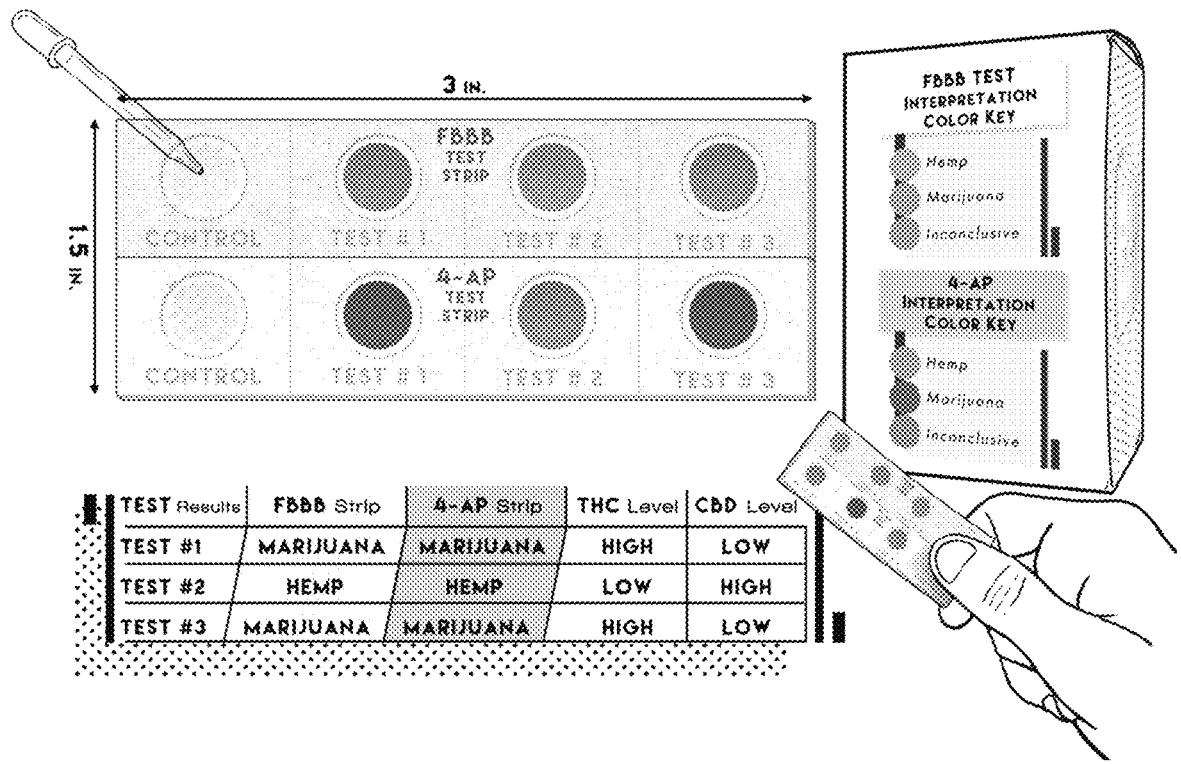
FIG. 3 shows a test strip combining two colorimetric reactions (FBBB and 4-AP) into a single test strip.

A colorimetric test strip can be used to visually differentiate between hemp and marijuana and can then, optionally, be subsequently transported to a laboratory for confirmatory analysis using GC-MS by direct thermal desorption of the substrate using a probe. The Fast Blue BB (FBBB) reaction with THC has been demonstrated to be sensitive (~50 ng detection) and produce a discernable color difference from the FBBB reaction with other cannabinoids, in particular cannabidiol (CBD). A depiction of the test strip combining two complementary reactions (FBBB and the 4-aminophenol) with both high THC content plant extracts and low THC content (but high CBD content) extracts is shown in FIG. 3.

The strip (FIG. 3) contains small reaction wells measuring between 3 mm-6 mm in diameter each. These wells contain circular sorbent-coated glass microfiber substrate materials (CMV-A and CMV-B) for the reactions and to deposit unreacted target analytes for subsequent thermal desorption into an analytical instrument. A series of three CMV substrates contain the pre-loaded FBBB reagent and another series of three CMV wells contain the preloaded 4-AP reagent loaded onto it. The remainder of the strip itself may be made of, for example, thick paper, plastic, or PDMS with the wells in it deep enough to allow the reagents to collect and react.

With this field kit, the user can conduct a ~1 mL solvent extraction of a small amount ~10 mg of the plant material. A small amount (~10 uL) of the solvent extract can be dropped into each well and the color reaction observed after adding a base. A red color in the FBBB well and blue color in the 4-AP well indicate marijuana while an orange color and pink color indicate that the plant is hemp. By testing the cannabis with both tests in parallel, the true positive and true negative rates increase and that the false positives and the false negative rates decrease.

Figure 4:
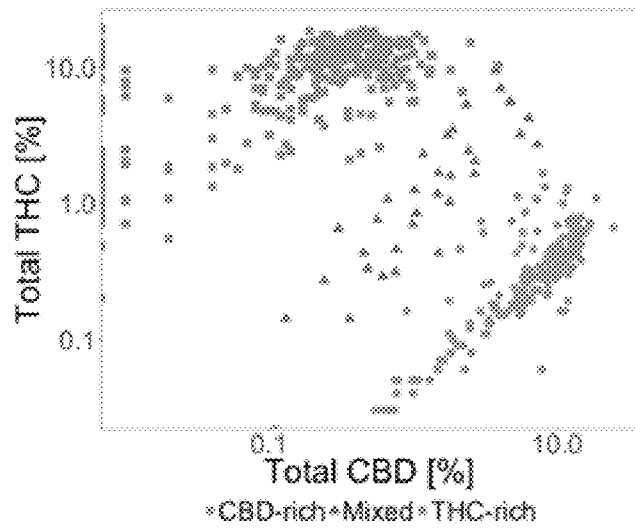
FIG. 4 shows the distribution of ~300 seized cannabis samples according to their total THC and CBD concentrations plotted on a Log 10 scale.

Receiver operating characteristic (ROC) curves can be used to evaluate the specificity vs sensitivity of each test by itself and when using both tests in combination for different testing parameters. While a small number of plant samples containing mixed THC/CBD levels are expected in seized suspect plants, potentially rendering an "inconclusive", the number of either low THC and low CBD or high THC and high CBD seized samples is expected to be low. The majority of the samples were clearly differentiated as either THC-rich or CBD-rich (FIG. 4).

Another version of the strip contains a series of wells with only the FBBB reagent previously loaded into the well and a "control" well (also containing a known amount of internal standard) to deposit the unreacted extract for subsequent instrumental analysis in the laboratory, if desired. The extraction and reaction steps would follow as above but this second type of strip can be evaluated as a potential test for total THC concentration based on color intensity.

The test can be accompanied by a color chart that displays the range of concentrations expected according to color intensities. The analytical figures of merit (LOD, precision, accuracy and uncertainty) of this strip can be evaluated for a potential total THC potency test of cannabis and reporting total THC along with an uncertainty estimate associated with the reported concentration. The added benefit of using the CMV as a substrate for these tests is that because CMVs can withstand high temperatures, the substrate can be analyzed through mass spectroscopic techniques, such as GC-MS and DART-MS to confirm both the target analytes (e.g., CBD and THC) and the chromophore that was visualized. Paper substrates on the other hand, have been found to burn easily and create background in the spectra, making it difficult to interpret the data.

Example 2—Colorimetric Tests of Different Extracts

Figure 5:
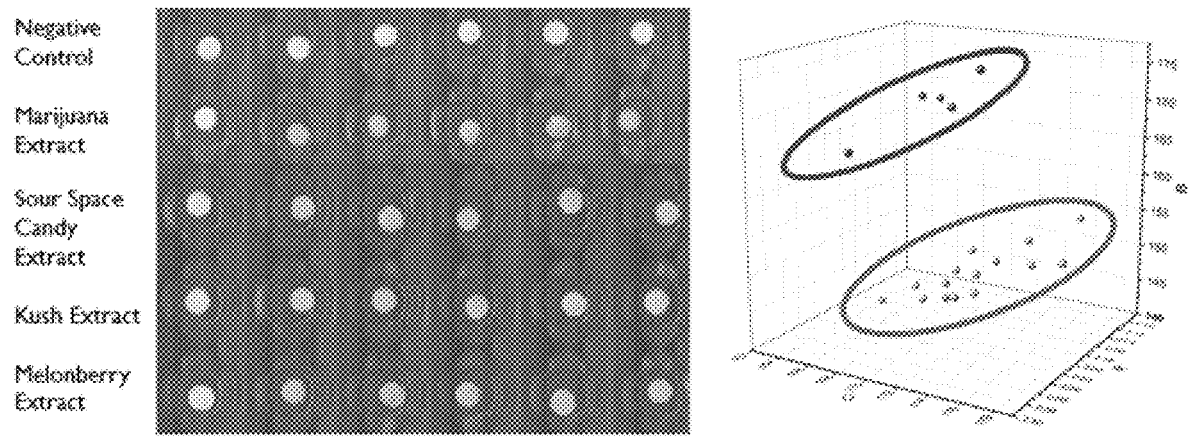
FIG. 5 shows the colorimetric reaction of marijuana and 3 hemp extracts with FBBB. Left: marijuana and 3 hemp extracts reacted with Fast Blue BB. Right: Scatter plot of the RGB codes obtained from the Marijuana+FBBB chromophore (red) and Hemp+FBBB chromophore (orange).

A 5 mm spot of the PDMS-coated glass substrate was pre-loaded with FBBB reagent and reacted with extracts from a marijuana plant (high THC) and with the extracts from three different commercially available hemp plants (low THC but high CBD content). FIG. 5 (left) illustrates the color differences between the product chromophores resulting from the reactions within the spot well on the substrate for the two types of cannabis extracts. FIG. 5 (right) shows a scatter plot of the RGB codes equivalent to the red and orange colors obtained from the Marijuana+FBBB chromophore and Hemp+FBBB chromophore, respectively. Mass loadings of THC and CBD as low as 100 ng produce a color change. These limits of detection are much lower than the expected concentrations of ~5-15% THC (w/w) in marijuana plants when ~5 mg of plant material is extracted with 0.5 mL of ethanol or similar solvent and a 10 uL of the ethanol extracts are added to the pre-loaded substrate followed by addition of 10 uL of a basic solution to produce the chromophores.

Figure 6:
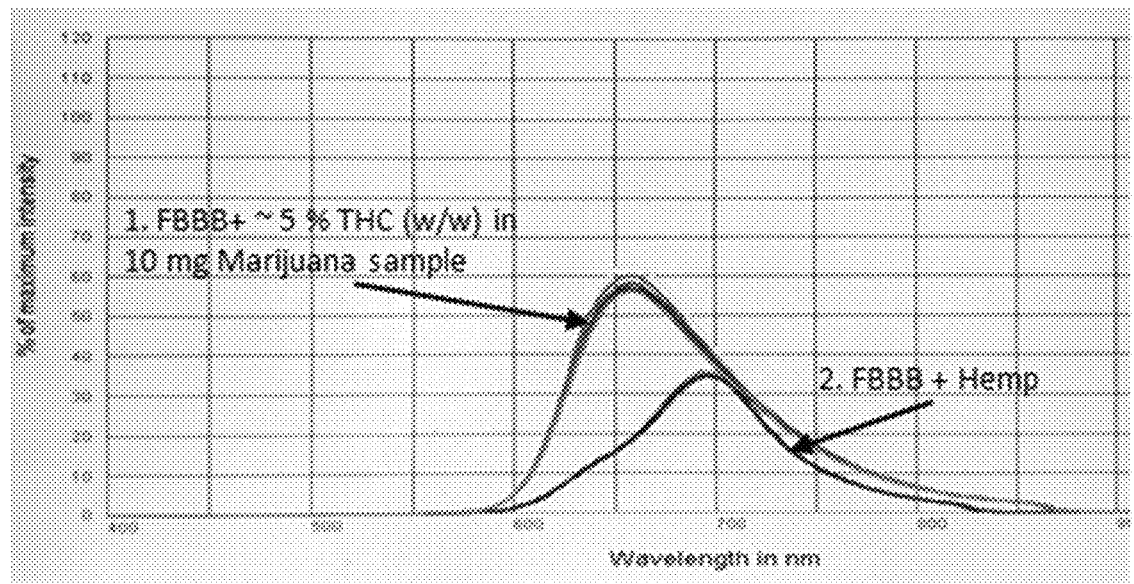
FIG. 6 shows fluorescence spectra obtained from two FBBB+Cannabinoid chromophores. 1) Color intensity equivalent to a 5 mg marijuana sample that is ~5% THC (w/w) extracted with 0.5 mL of ethanol and 2) 0.5 mL ethanol extraction of hemp, (expected to contain low THC but high CBD). The replicate spectra were obtained by irradiating a 5 mm spot of the CMV with a 400-540 nm spotlight source. The CMV was pre-loaded with FBBB reagent and 10 uL of the ethanol extracts were added followed by addition of 10 uL of a slightly basic solution to produce the chromophore.

Fluorescence spectra obtained from two FBBB+Cannabinoid chromophores are shown in FIG. 6. The intensities are equivalent to a reaction from the extracts of 5 mg samples (~5% THC and ~5% CBD) extracted with 0.5 mL of ethanol and 10 uL of the ethanol extracts added to the pre-loaded 5 mm substrate spot followed by addition of 10 uL of a slightly basic solution to produce the chromophores.

Example 3—Colorimetric Tests in Different Supports

The color reaction from FBBB and cannabinoids ($\Delta^9$-THC, CBN, and CBD) was performed by observing a reddish color change with the naked eye in three-different strips support paper, CMV-A, and CMV-B. For strips of filter paper, the $\Delta^9$-THC, CBN, and CBD were detected at 50 ng mass loadings.

While using the strips of CMV-A and CMV-B mass loadings of 100 ng for all cannabinoids tested were detected when compared with the blank. In the fully assembled, multi-strip CMV-A and CMV-B devices, the reddish color was observed with 500 ng mass loading of each compound.

The presumptive test commonly used by many forensic laboratories to identify marijuana is the Duquenois-Levine test with reported detection limits of 5 μg (5000 ng) for THC. The polar characteristics of the paper, due to hydroxyl groups present in cellulose, caused more diffusion in methanolic solutions utilized in all experiments while the CMV-A had less diffusion between all of the supports tested. On the other hand, CMV-B is functionalized with methyl groups and is more polar. The CMV-A and CMV-B strips have more surface area due to their 3D structure, which allows more quantitative adsorption. The sensitivity decrease from a single CMV strip to the fully assembled CMV device is a result of the detectable minimum concentration increase on the devices (CMV-A and CMV-B) due to the presence of seven strips in the glass filter. This result showed the use of the CMV-A and CMV-B as a rapid colorimetric test device, which can then be used directly for GC/MS studies.

Example 4—False Positive Tests with Fast Blue BB

The false-positive results from methanol, methylene chloride and water extracts for eight teas, three hemp varieties, and two hop varieties are given in Table 2.

TABLE 2

Result of different tea, hemp, and hops extracts against solution of FBBB.

| Sample | MeOH | $CH_2Cl_2$ | $H_2O$ |
|---|---|---|---|
| Bag 1 - Peppermint | − | − | − |
| Bag 2 - Green Tea | + | − | + |
| Bag 3 - Tazo ®: Chamomile flowers, hibiscus flowers, spearmint leaves, rose petals, lemongrass, blackberry leaves, peppermint leaves, sarsaparilla root, lemon balm leaf, licorice root | + | − | + |
| Bag 4 - Tazo ®: hibiscus flowers, licorice root, orange peel, cinnamon, rose hips, lemongrass, fruit juice extract | + | − | + |
| Bag 5 - PUKKA ®: Oat flowers, licorice root, Chamomile flowers, lavender flowers, limeflowers, valerian root, green Rama tulsi leaf | + | − | + |
| Bag 6 - Black tea | + | − | + |
| Bag 7 - Twining ®: Tea, natural citrus and tea flavorings with other natural flavorings, tea extracts | + | − | + |
| Bag 8 -Throat Coat ®: licorice root, slippery elm bark, marshmallow root, wild cherry bark - Prunnus serotine, fennel fruit, cinnamon bark, sweet orange peel | + | + | + |
| Blue Ridge Hemp-Sour Space Candy Strain Blue Ridge Selects Flower | − | − | + |
| Blue Ridge Hemp - Kush Hemp Strain Outdoor Connoisseur Blue Ridge Selects Flower | − | − | − |
| Blue Ridge Hemp - MelonBerry Strain Blue Ridge Selects Flower | − | − | − |
| BSG ™ Hops- Azacca ® Hop Pellets | + | − | + |
| LD Carlson- Apollo ® Hop Pellets | − | − | + |
| Yamacha Chief Hop Union - Citra Whole Leaf Hops | − | − | + |

(+) positive result and (−) negative result.

Except for sample bag 1, all methanol and water extracts of the teas gave positive results with the FBBB reagent, exhibiting a false-positive result if testing for cannabinoids. With the methylene chloride extract, sample 8 gave a positive result, while all others gave negative results. Out of all the hemp results, the only false positive that was observed was from the water extract of Sour Space Candy Strain. False positives were also observed for the water extracts for all hop products as well as the Methanol extract for the Azacca hops pellets. Phenolic compounds are more soluble in polar solvents like methanol and water, due to the strong interaction between the hydroxyl groups by hydrogen bonds. Methanol is also a non-selective solvent and could extract other compounds from plants while the non-polar solvent (methylene chloride) is more selective for non-polar compounds.

It should be noted that for all three hemp samples, methylene chloride and methanol extracts produced a deep orange color, indicating a high concentration of CBD. This shows that FBBB could be used to differentiate between hemp and marijuana due to low levels of THC and high levels of CBD in hemp. This test is preferably conducted using a non-polar solvent such as chloroform, methylene chloride, hexane and others to minimize the occurrence of false-positive results.

Example 5—DART(+)MS and DART(+)MS/MS

The confirmation of the chromophore through DART-MS gives an accurate confirmation of the FBBB+THC chromophore in 2 minutes as opposed to 20 minutes in standard GC-MS run.

DART(+)MS analysis allowed the formation of the products between FBBB and all cannabinoids standard solutions as a function of different heating temperatures (300 and 400° C.), collision energies (0, 30, 60 and 120 V) and the three supports proposed. All products that formed are identified, shown in FIG. 7.

The nominal average mass of FBBB is 312 Da, but its mass spectra showed only fragments at m/z 286.13 and 300.13. The m/z 286.13 is due to loss of the nitrogen portion ($N_2$) in gas form due to the instability of the diazonium ion. This loss is followed by the substitution of hydrogen and the detection occurs by protonation of the nitrogen in the amide group. The m/z 300.13 is due to the substitution of the diazonium anion by positive charged oxygen. The ionization by DART(+)MS was realized with He gas in high temperatures (300 and 400° C.), producing metastable He atoms.

Figures 7E, 7F:
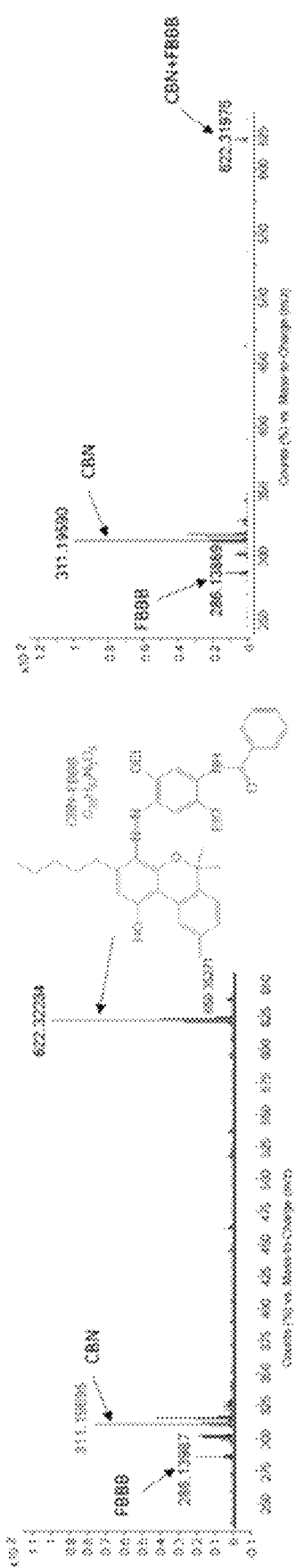

In ambient atmosphere, the metastable He atoms can interact with other molecules such as nitrogen, oxygen, water and basically any other gaseous species including the analyte molecules. Besides, the ionization mechanism can occur via penning ionization, i.e., forming molecular-ion or by proton transferring ([M+H]$^+$). In this context, the DART (+)MS ionized chromophores via M.$^+$ species. However, the high temperature of DART source can provoke degradation reactions of FBBB reagent, principally due to diazonium ion portion. The chromophore produced between FBBB with $\Delta^9$-THC, CBD and CBN show molecular-ions (M.$^+$) at m/z 626.35302; 626.35346 and 622.3223, respectively, as well as the reagents cannabinoids, are detected as [M+H]$^+$ ions (FIG. 7).

The DART(+) mass spectra show that the reagents (FBBB and cannabinoids) are more intense at a heating temperature of 400° C., whereas the chromophores produced are more intense at 300° C., where degradation products are not observed. In DART analysis, the increase of temperature accelerates the release of reagents from support surface to gas phase. This process is favored by increase of MW values and/or polarity. But some of the supports may be problematic because they do not tolerate the high temperature and have matrix interference. The paper support, for instance, darkened at 400° C. due to degradation. On the other hand, the CMV-A and CMV-B devices did not change color and there was less background during the analysis.

Figure 8:
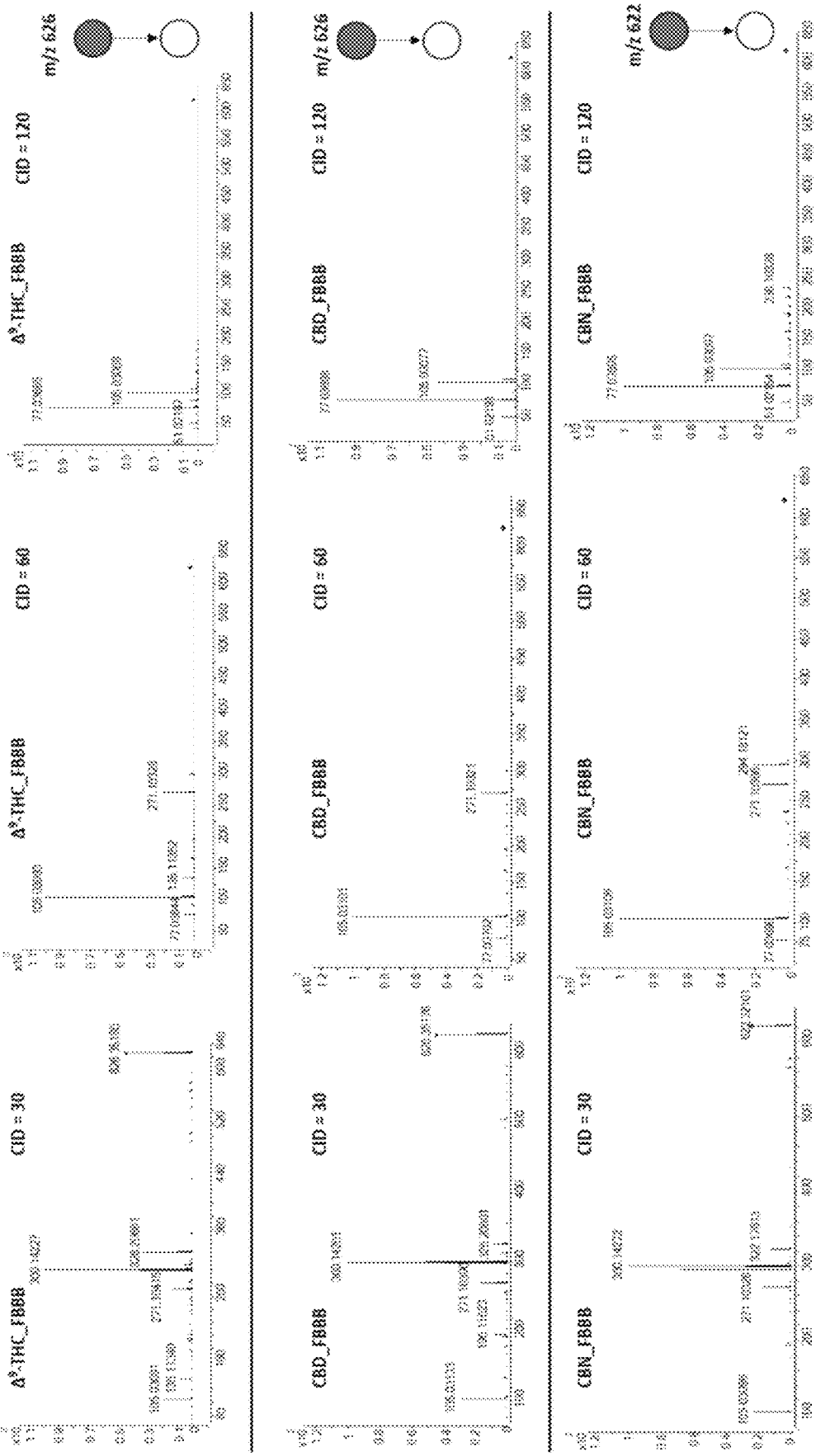
FIG. 8 shows CID experiments performed in a Q-TOF with collision energy of 0, 30, 60 and 120 V for all chromophore produced from reactions between cannabinoid standards and FBBB. The CID experiments were performed in DART(+) source at 400° C.

The DART(+)MS/MS results were performed with collision energy varying from 0 to 120 V for the ions m/z 626.35302; 626.35346 and 622.32235 acquired for all chromophores with the aim to examine the reaction between FBBB and cannabinoids, FIG. 8. The DART(+)MS/MS for all chromophore showed a standard fragmentation. In CID with 0 V of collision energy, no fragmentation was observed. However, when the value is increased to 30, 60 and 120 V, main fragments are formed at m/z 300.14; 105.03 and 77.03, respectively. The CID in 30 V shows more fragments from the m/z precursor, i.e., parent ions. For the $\Delta^9$-THC plus FBBB chromophore, other fragments are observed at m/z 326.20 (CID 30 V) 271.10 (CID 30 and 60 V); 135.11 (CID 30 and 60 V) and 51.02 (CID 120 V). The m/z 105.0 appeared at CID 30, 60 and 120 V collision energy for all chromophores. The CBD plus FBBB chromophore has a similar fragmentation profile to $\Delta^9$-THC plus FBBB chromophore. However $\Delta^9$-THC plus FBBB fragmentation is a little different in relation to CBD plus FBBB chromophore, which has an additional peak at m/z 196.11623. CID spectrum of CBN plus FBBB chromophore allows the identification of other fragments at m/z 322.17 (CID 30), 294.18 (CID 30 and 60) and 51.02 (CID 120), FIG. 8.

Figure 9:
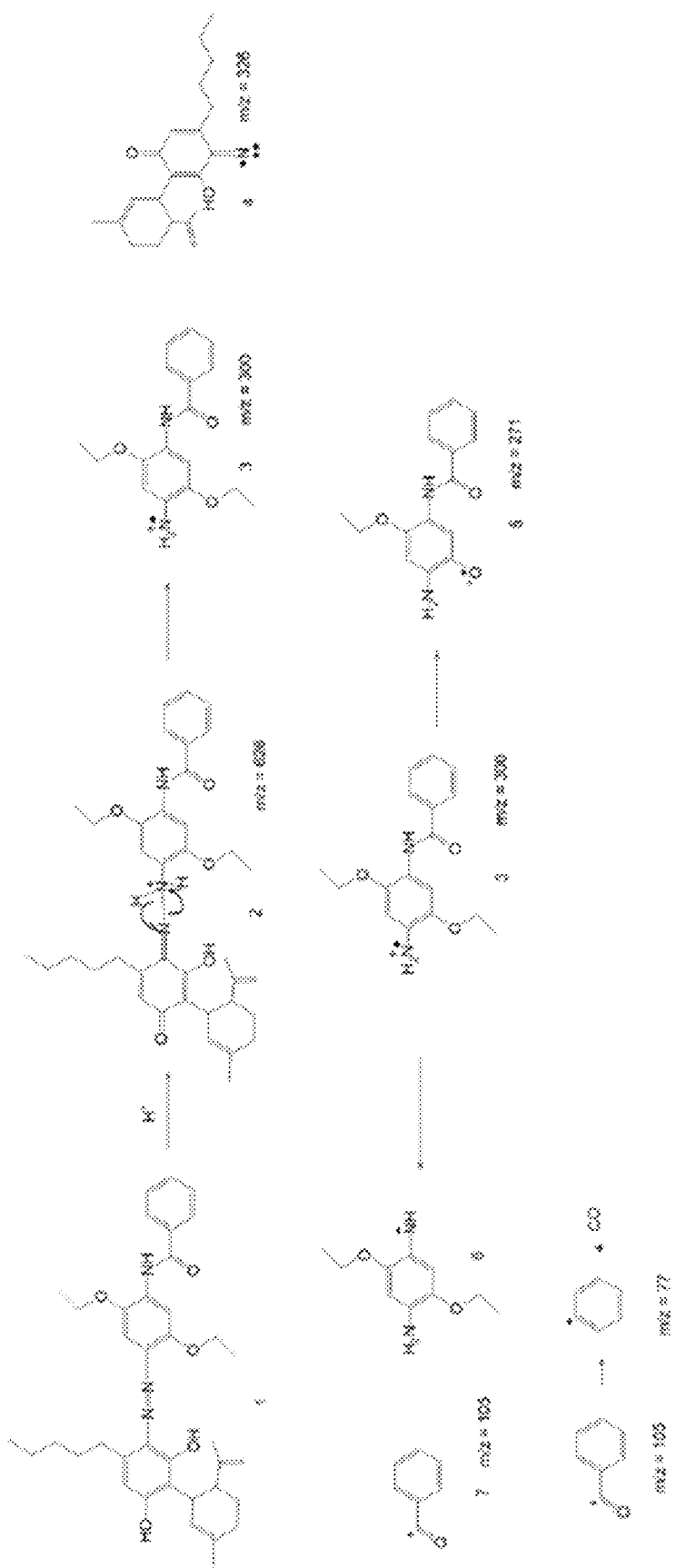
FIG. 9 shows fragmentation proposed for the ion of m/z 626 using DART(+)MS/MS. The rotes a, b, and c were constructed from CID experiment at 30 V.

Using the chromophore from CBD and FBBB, for example, the ion of m/z 626, in its tautomeric form, as compound 2, eliminated the main radical fragment at m/z 300 (3), FBBB portion, and in lower intensity the cannabinoid portion at m/z 326 (4), due to the cleaved bond between the nitrogen atoms. The CBN part was observed in the fragmentation as ions of m/z 322. After, the ion of m/z 300 has two different ways of fragmentating, one gave the ion of m/z 271 (5) that was obtained by elimination of ethyl radical in the ortho position to amine and other gave the ions at m/z 196 (6) and 105 (7), which were formed by a bond cleavage in amide functional group between the carbonyl and the amine group (FIG. 9). When collision energy increases, the fragmentation pattern changes, where fragments with lower m/z values are mainly produced, such as m/z 105 and 77 when energy values of 60 and 120 V are applied, respectively.

Example 6—$^1$H NMR Analysis of the Chromophore from $\Delta^9$-THC and FBBB

Figure 10:
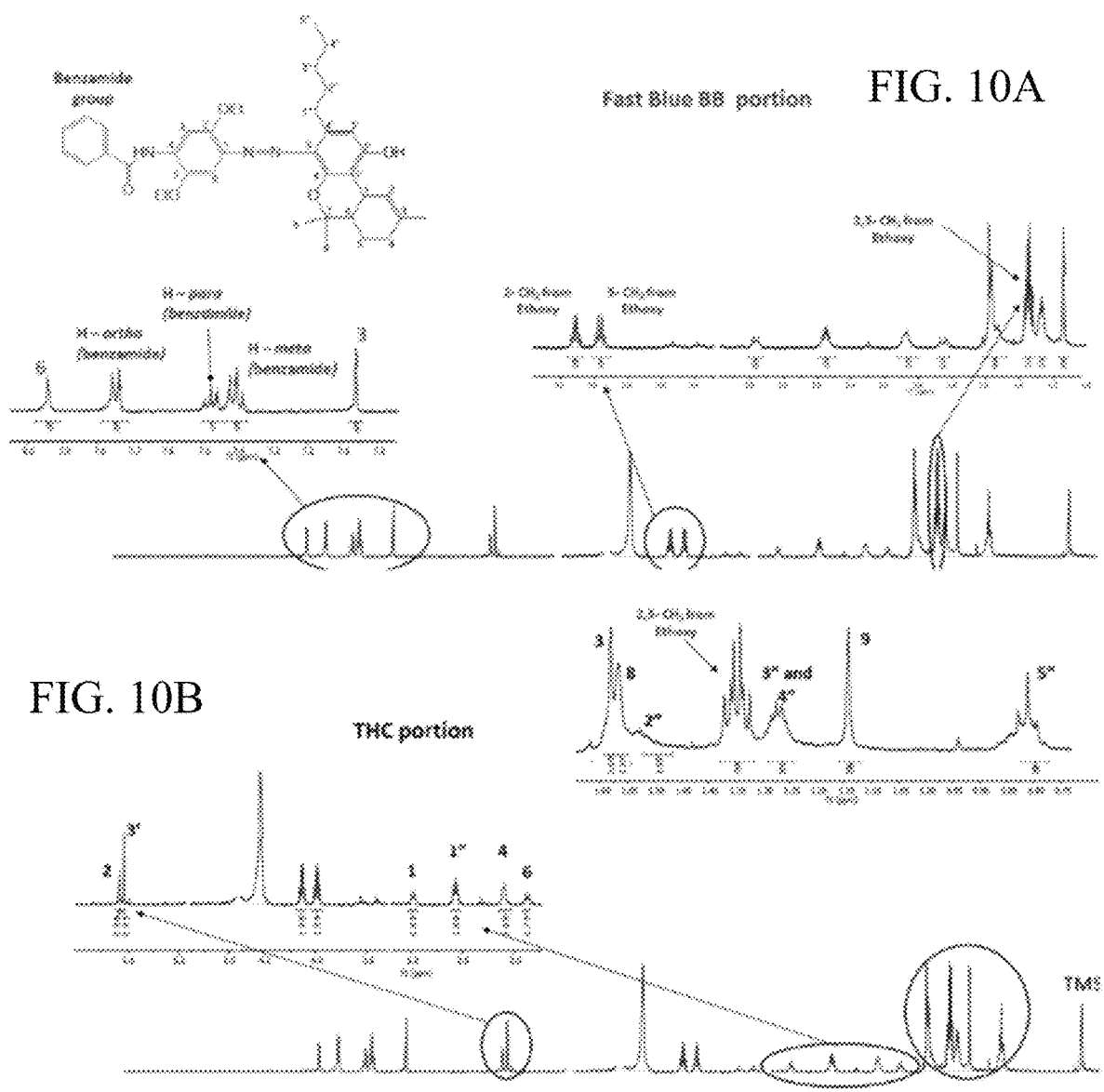
FIGS. 10A-10B show the $^1$H NMR spectrum of the $\Delta^9$-THC plus FBBB. A—spectrum corresponds to chemical shift of FBBB portion of chromophore and B—part of spectrum represents the $\Delta^9$-THC portion.

The TLC analysis allows observation that the reaction between $\Delta^9$-THC and FBBB produce two major intense bands of red color, with retention factors (Rf) of 0.15 and 0.51. The purification process by column chromatography leads to the isolation of the main compound in Rf 0.15 (10 mg yield in 18 mg of a total reaction; fractions between 35 and 38) and impure fraction from the band in Rf 0.51 (5 mg yield in 18 mg of a total reaction; fractions between 14 and 24). These compounds were studied by 1D and 2D $^1$H NMR analysis as well as a direct injection in DART(+)MS, and showed that the compound in Rf 0.15 was totally pure (FIG. 10 and Table 1).

The $^1$H NMR spectrum showed seven different signals with chemical shift (δ) range from 7.94 to 7.06 ppm, due to aromatic protons from the FBBB portion (FIG. 10B). Two singlet peaks were observed in 7.94 and 7.06 ppm regarding aromatic proton in ortho and meta position of the azo group, respectively. The methylene proton signal from ethoxy groups were observed at 4.11 ppm (q, J=6.8 Hz, 2H) in the ortho position and 3.97 ppm (q, J=7.0 Hz, 2H) in the meta position. Both methylene protons were coupling with respective methyl groups in 1.35 ppm (TD, J=7.0, 4.8 Hz, 6H). The coupling between hydrogens from the ethoxy group was confirmed by analysis of homonuclear correlation spectroscopy—COSY.

Continuing the analysis of the FBBB molecular part of the chromophore, from the benzamide group, a multiplet with chemistry shift in the 7.78-7.73 ppm range due to the hydrogens in the ortho position. The protons in the meta position showed a signal in 7.40 ppm and coupling constant typical of ortho position (dd, J=8.1, 6.7 Hz, 2H). Multiplet signal in 7.47 ppm is due to a proton in the para position. The $^1$H NMR analysis for FBBB pure was done to compare with the chromophore data.

The $^1$H NMR analysis of the $\Delta^9$-THC portion of the chromophore showed singlet signal of the chemical shift in 6.02 ppm relative to the H-3' of the aromatic ring. The hydrogen signal from H-5' position was not observed due to the diazonium ion of FBBB reacting in the para position, leading to the most stable compound. This signal in THC appears in the chemical shift 6.27 (1H, d, 1.6 Hz). In 6.07 ppm, this signal was from the H-2 olefinic functional group of $\Delta^9$-THC, and the $^1$H-$^1$H-COSY spectrum showed the long-range coupling to the methyl group in the 3 position (s, 3H; 1.58 ppm) and methylene of the ring in H-4 (m, 2H, 2.07 ppm). The $\Delta^9$-THC is linked to another molecule (FBBB) leading to a different compound chromophore.

The H-1 exhibited a chemical shift of 2.97 ppm (d, J=10.8 Hz, 1H) and coupling constant value typical of trans configuration in relation to signal of the H-6 in 1.85 ppm (d, J=12.5 Hz, 1H). The $^1$H-$^1$H-COSY spectrum showed that H-1 also coupled with the methyl group in the 3 position of $\Delta^9$-THC, while the H-6 coupled with H-5 in 1.33 ppm. Two angular methyl groups showed singlet in 1.57 and 1.14 ppm for C8-methyl and C9-methyl groups, respectively.

Figure 11:
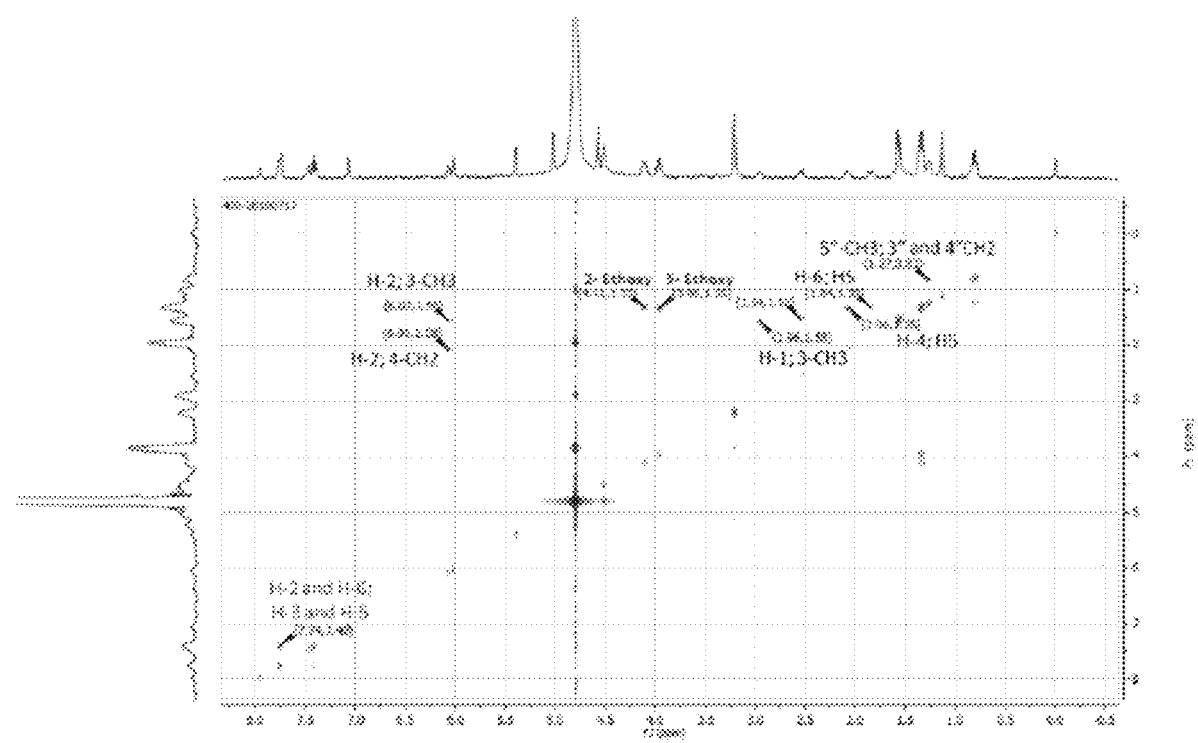
FIG. 11 shows the 1H-1H COSY spectrum of the D9-THC plus FBBB chromophore showed coupling of the FBBB (in red color) and D9-THC portions (in black color).
Figure 12:
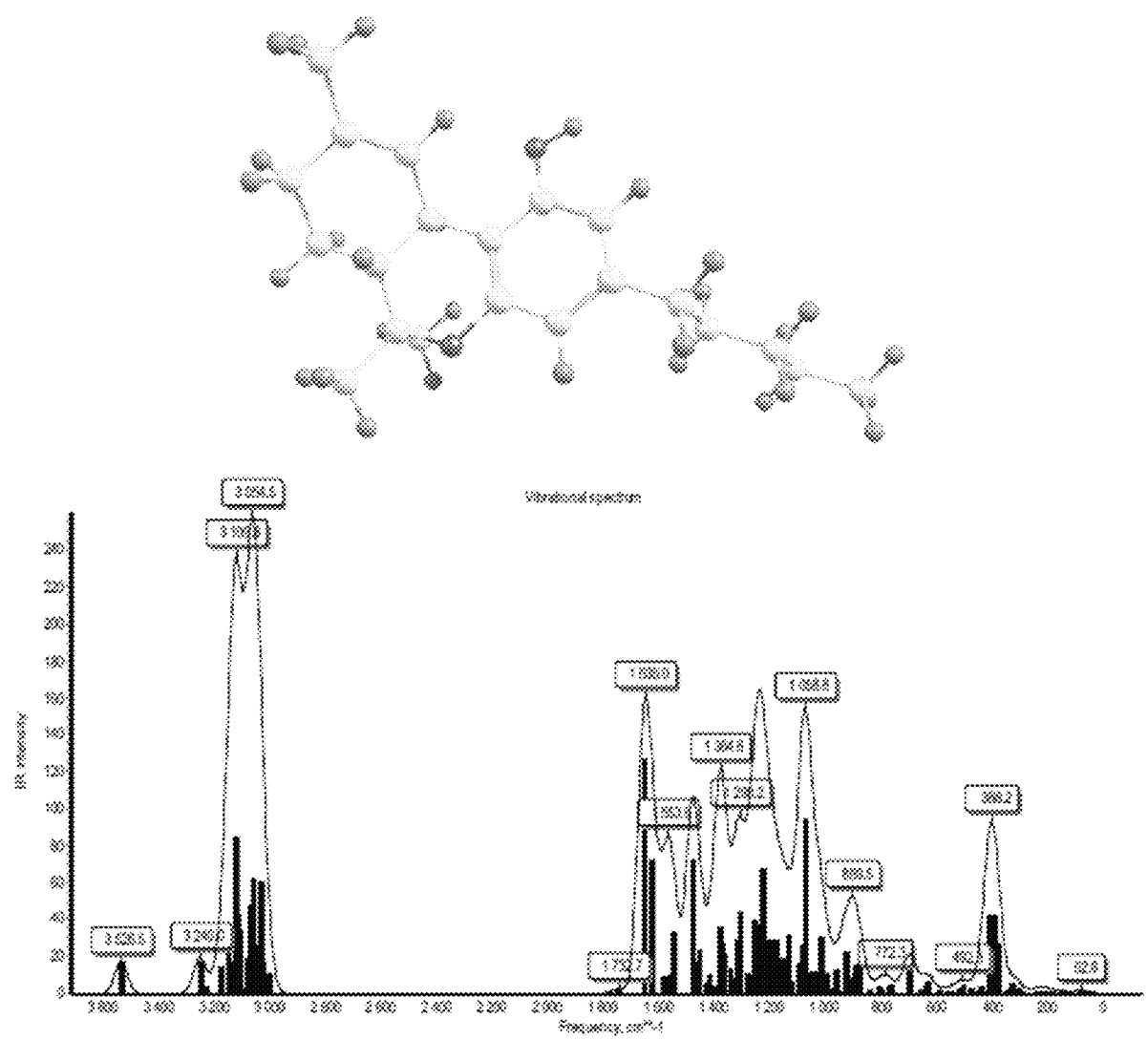
FIG. 12 shows the image of 3D structure, and IR Spectra of reactant THC (Zero point vibrational energy: 296.843 kcal/mol, Total Enthalpy: 311.993 kcal/mol).
Figure 13:
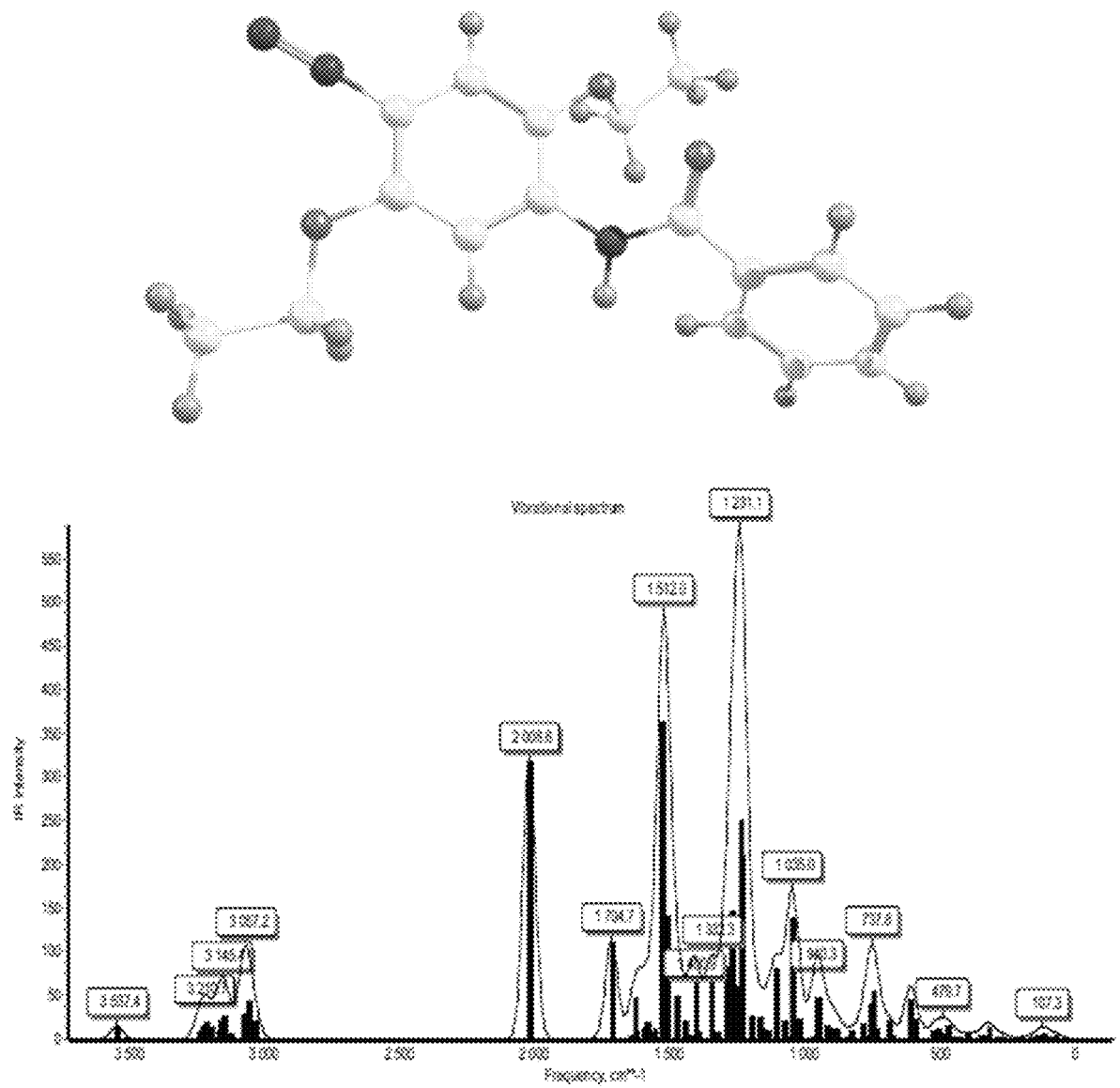
FIG. 13 shows the image of 3D structure, and IR Spectra of reactant Fast Blue BB (Zero point vibrational energy: 206.610 kcal/mol, Total Enthalpy: 221.043 kcal/mol).
Figure 14:
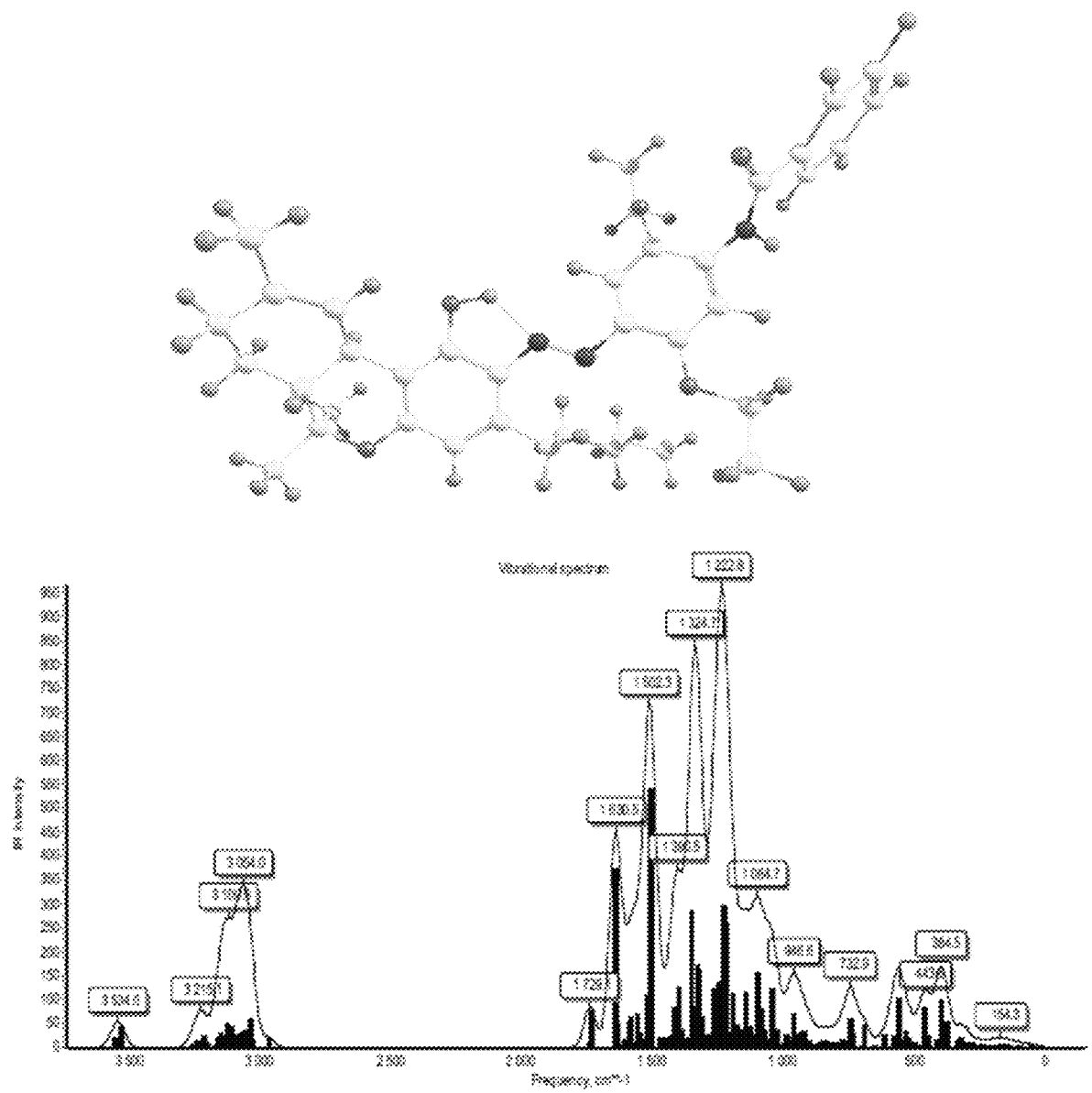
FIG. 14 shows the image of 3D structure, and IR Spectra of product t-bb-o (ortho-coupled product from THC+Fast Blue BB) (Zero point vibrational energy: 499.085 kcal/mol, Total Enthalpy: 528.093 kcal/mol).
Figure 15:
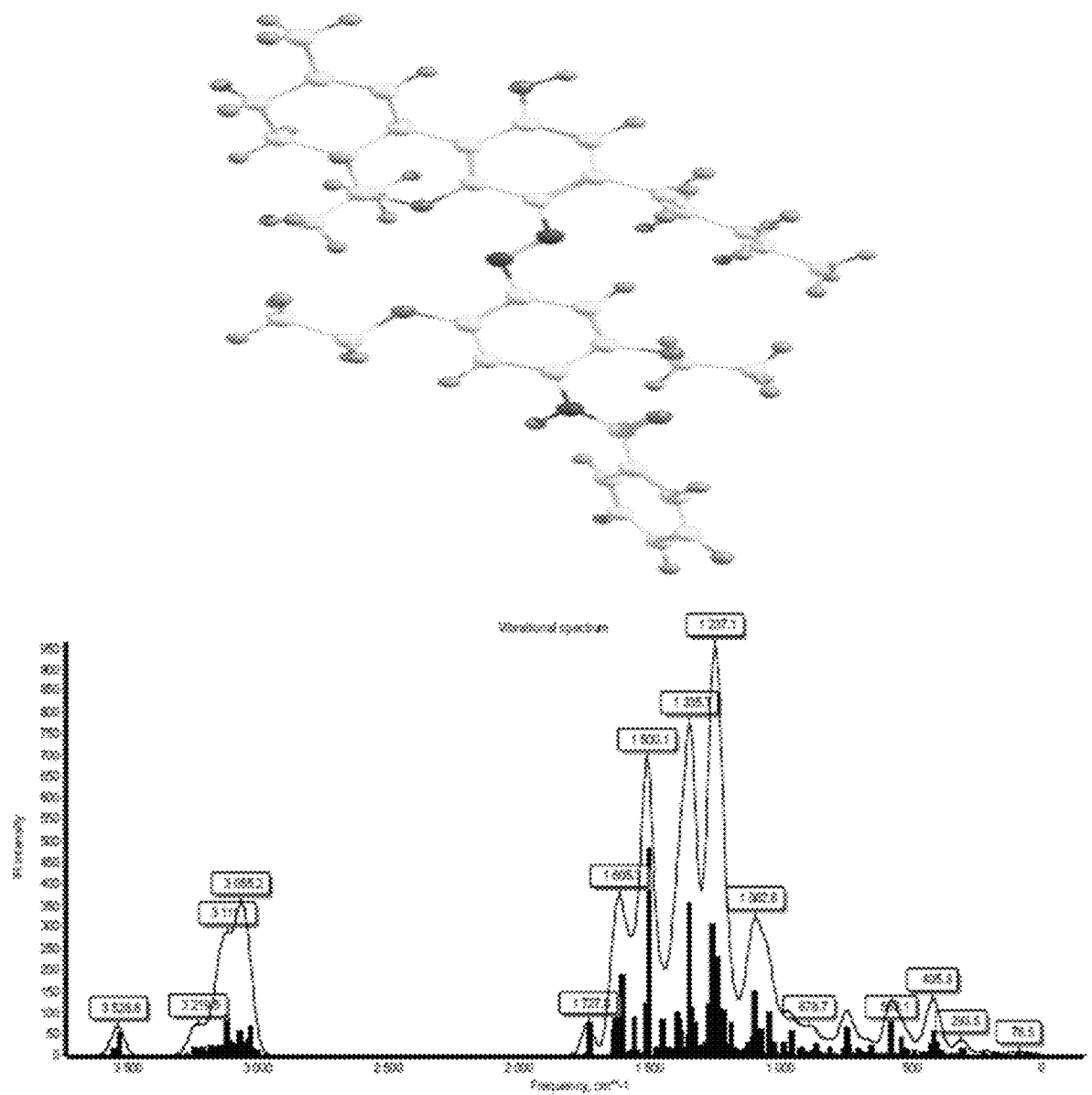
FIG. 15 shows the image of 3D structure, and IR Spectra of product t-bb-p (para-coupled product from THC+Fast Blue BB) (Zero point vibrational energy: 498.542 kcal/mol, Total Enthalpy: 527.760 kcal/mol).
Figure 16:
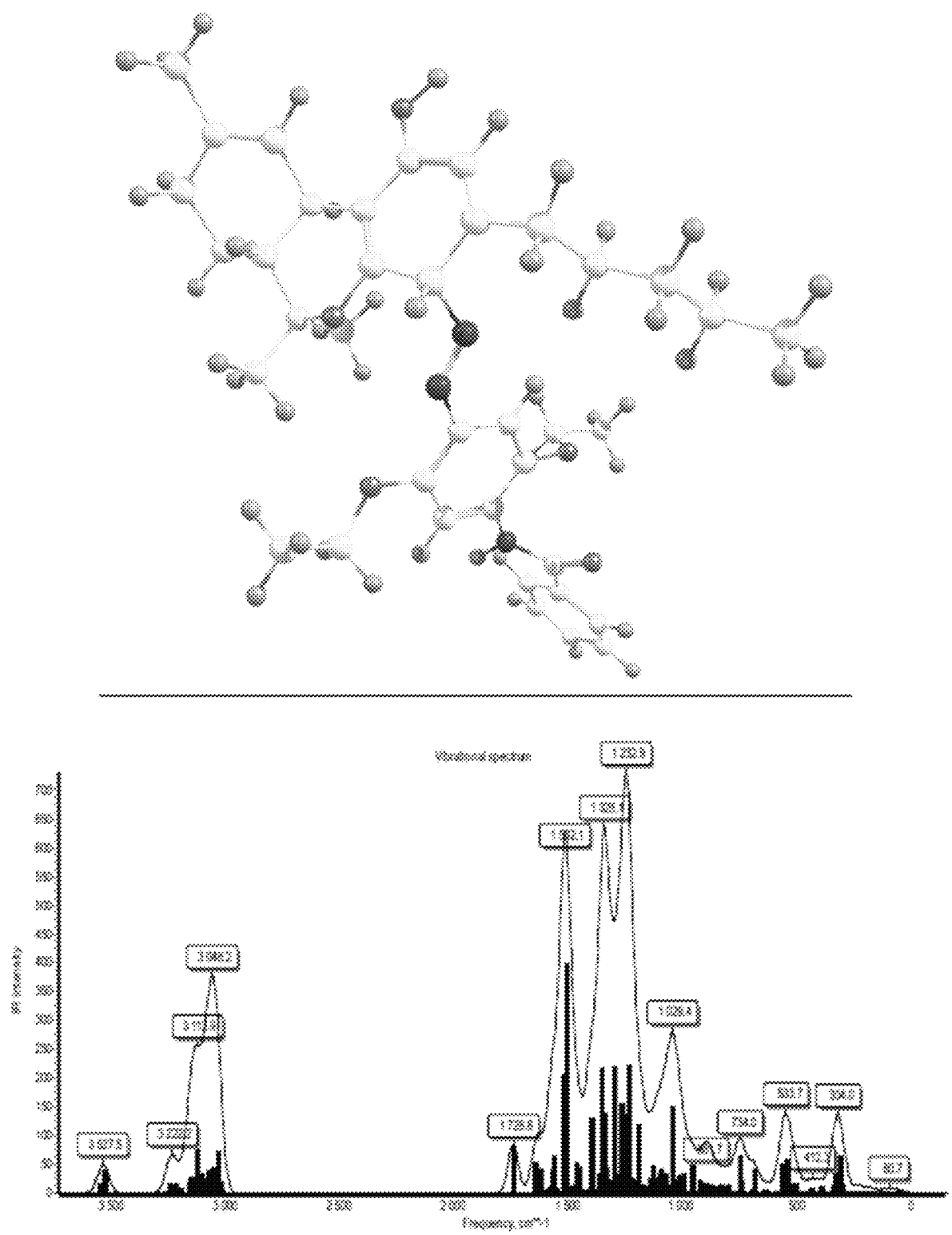
FIG. 16 shows the image of 3D structure, and IR Spectra of Intermediate t-bb-1-p (para-coupled intermediate from THC+Fast Blue BB) (Zero point vibrational energy: 503.897 kcal/mol, Total Enthalpy: 533.623 kcal/mol).
Figure 18:
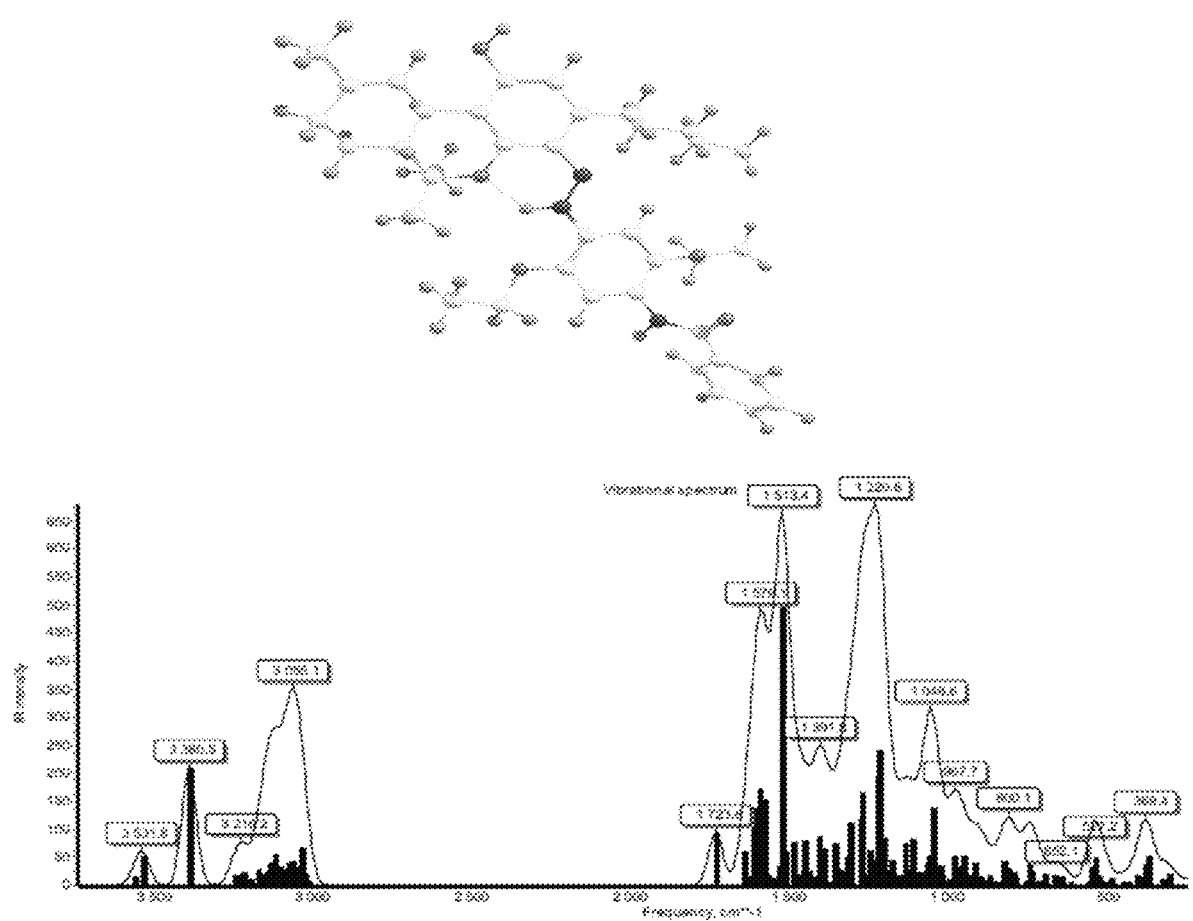
FIG. 18 shows the image of 3D structure, and IR Spectra of Intermediate t-bb-3-p (para-coupled intermediate from THC+Fast Blue BB) (Zero point vibrational energy: 506.249 kcal/mol, Total Enthalpy: 535.554 kcal/mol).
Figure 19:
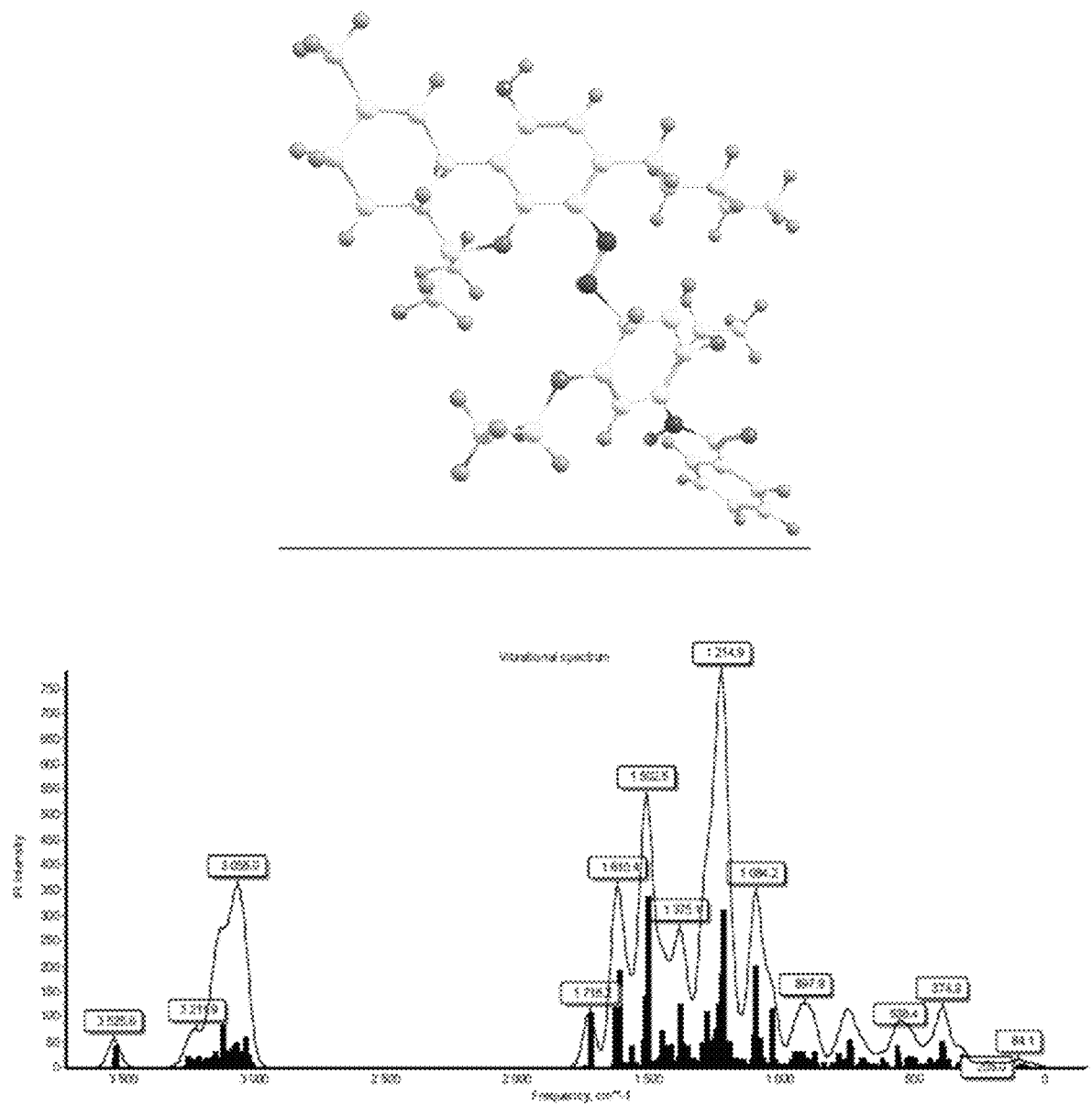
FIG. 19 shows the image of 3D structure, and IR Spectra of Intermediate t-bb-4-p (para-coupled intermediate from THC+Fast Blue BB) (Zero point vibrational energy: 503.648 kcal/mol, Total Enthalpy: 533.410 kcal/mol).
Figure 20:
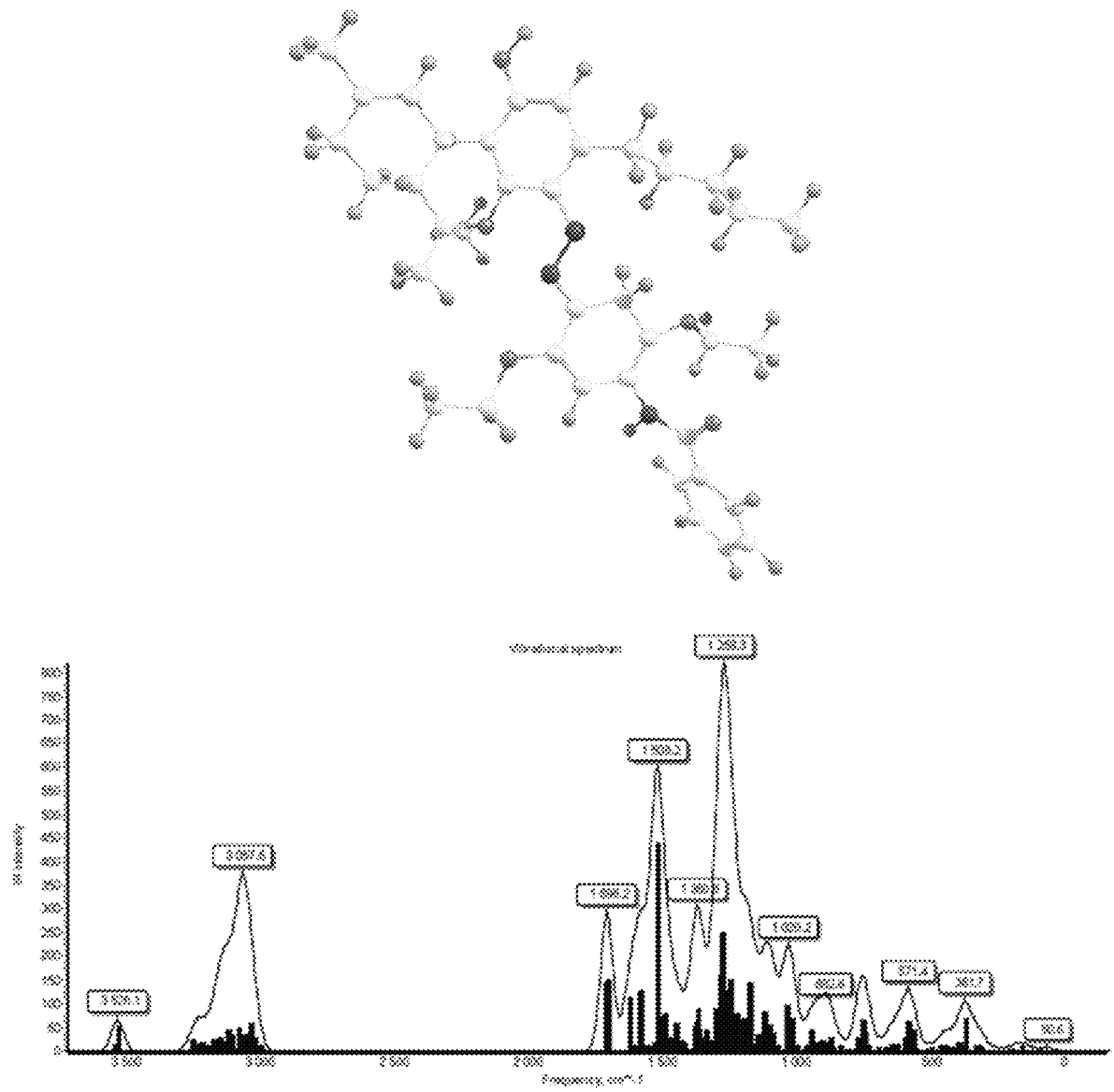
FIG. 20 shows the image of 3D structure, and IR Spectra of Intermediate t-bb-5-p (para-coupled intermediate from THC+Fast Blue BB) (Zero point vibrational energy: 505.405 kcal/mol, Total Enthalpy: 534.586 kcal/mol).
Figure 21:
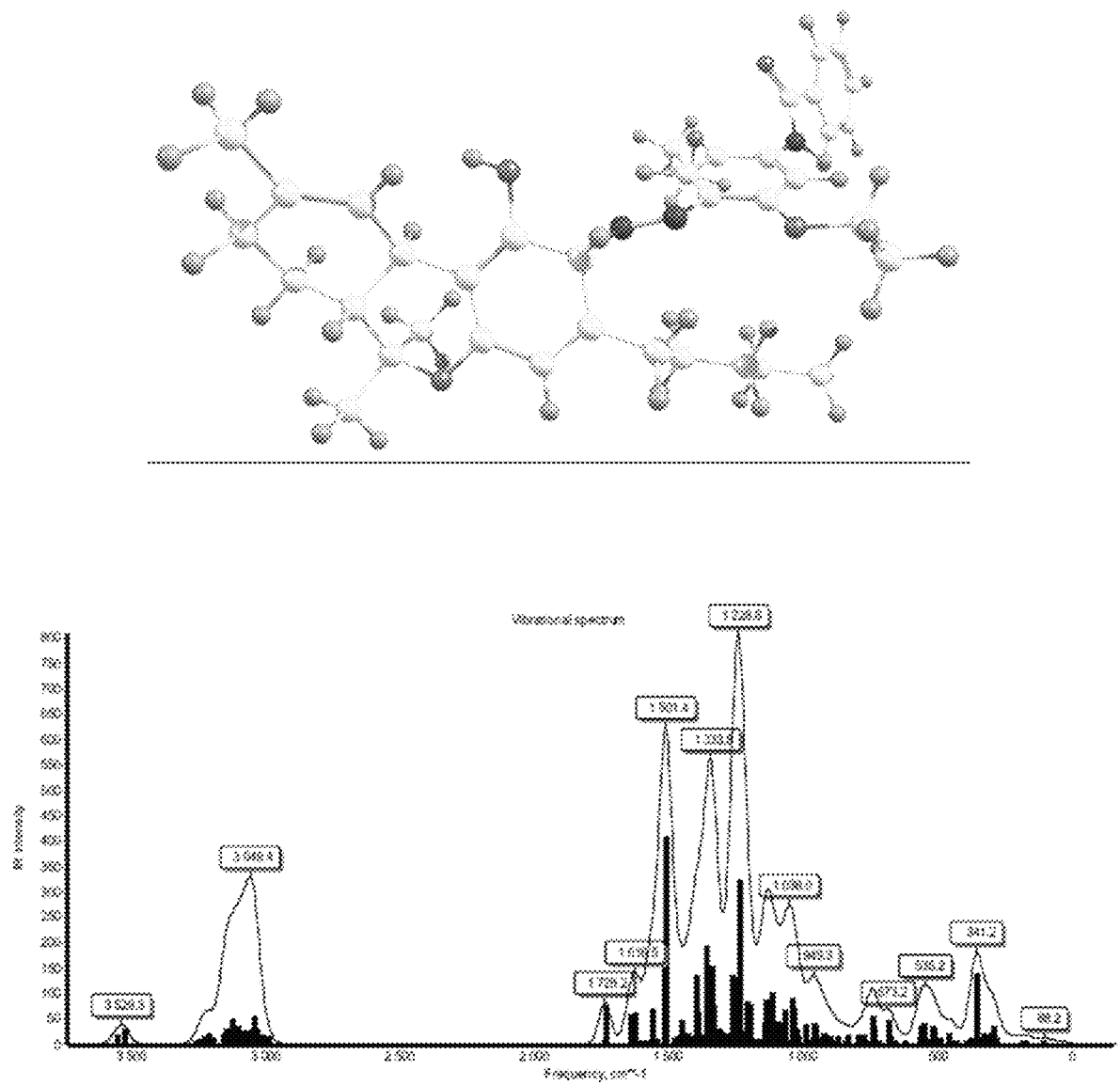
FIG. 21 shows the image of 3D structure, and IR Spectra of Intermediate t-bb-1-o (ortho-coupled intermediate from THC+Fast Blue BB) (Zero point vibrational energy: 504.523 kcal/mol, Total Enthalpy: 534.126 kcal/mol).
Figure 22:
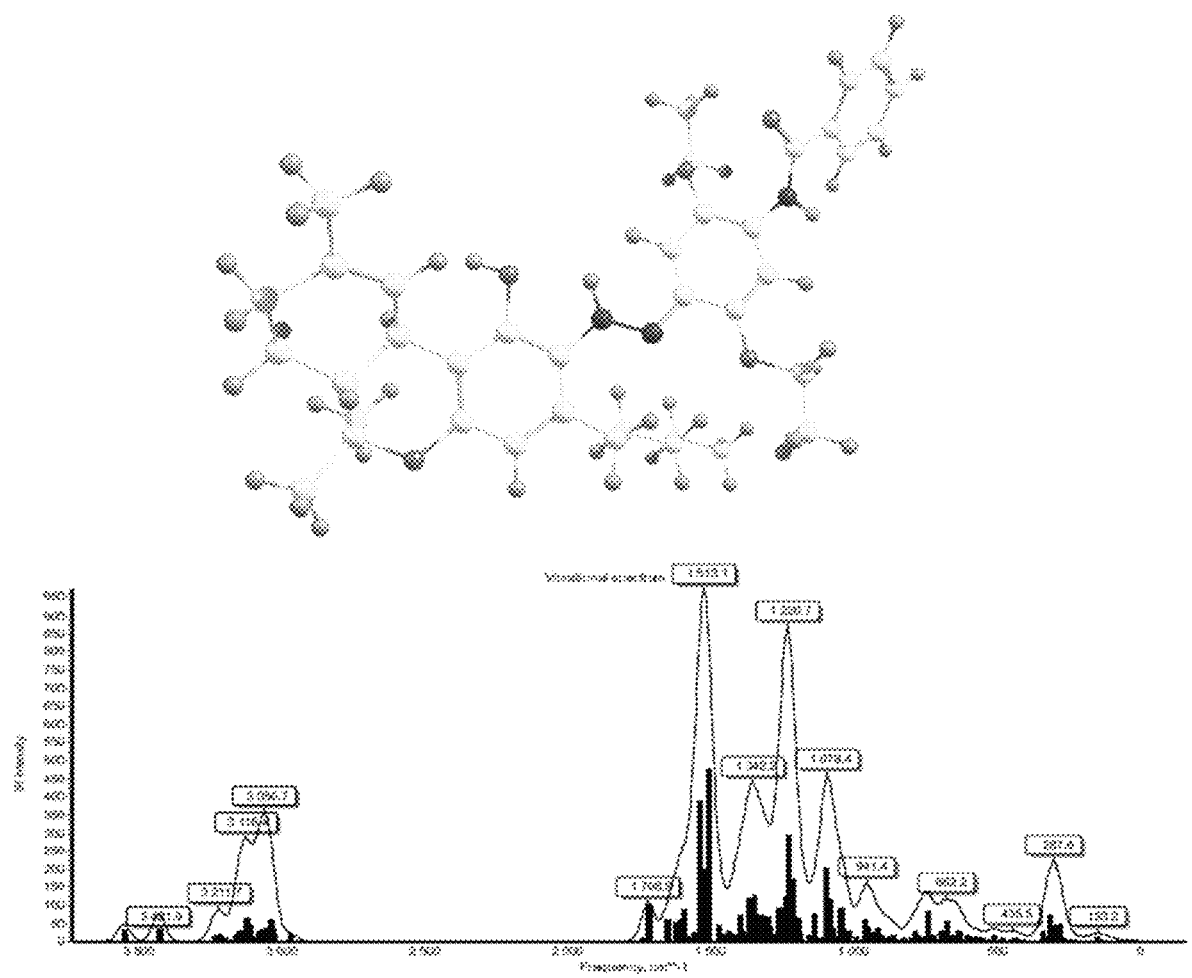
FIG. 22 shows the image of 3D structure, and IR Spectra of Intermediate t-bb-2-o (ortho-coupled intermediate from THC+Fast Blue BB) (Zero point vibrational energy: 506.513 kcal/mol, Total Enthalpy: 535.627 kcal/mol).
Figure 23:
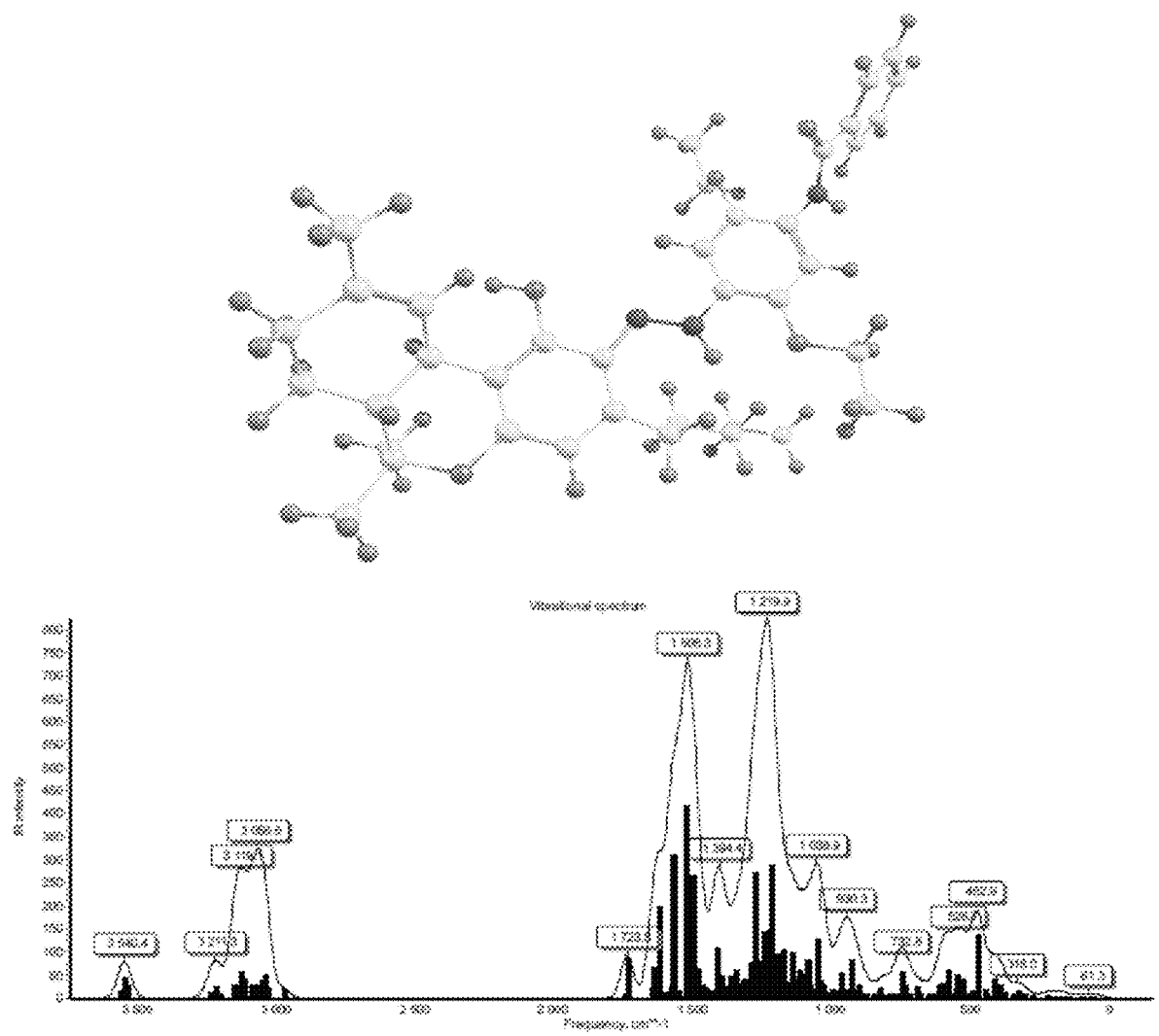
FIG. 23 shows the image of 3D structure, and IR Spectra of Intermediate t-bb-3-o (ortho-coupled intermediate from THC+Fast Blue BB) (Zero point vibrational energy: 505.783 kcal/mol, Total Enthalpy: 535.215 kcal/mol).
Figure 25:
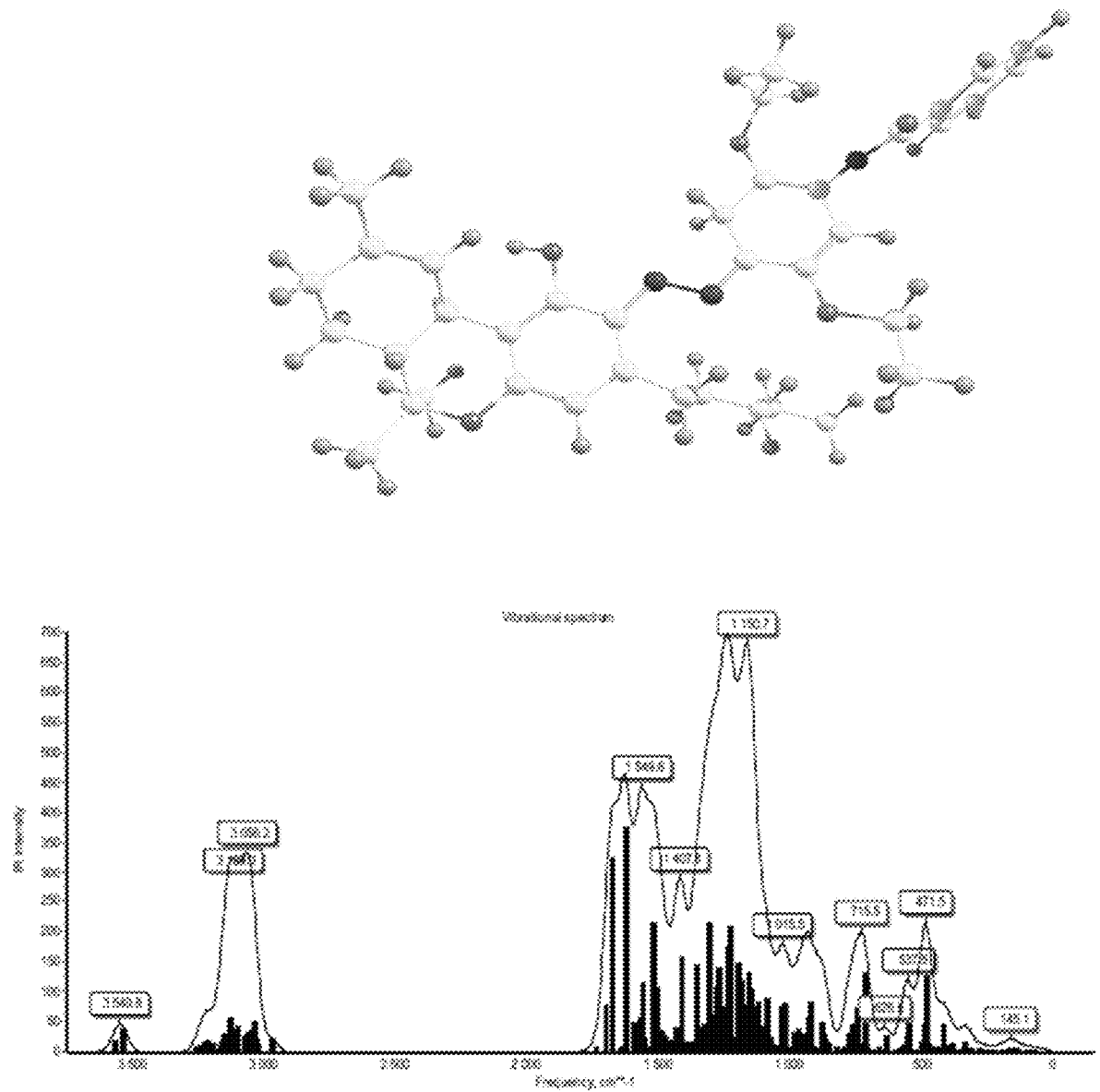
FIG. 25 shows the image of 3D structure, and IR Spectra of Intermediate t-bb-5-o (ortho-coupled intermediate from THC+Fast Blue BB) (Zero point vibrational energy: 505.267 kcal/mol, Total Enthalpy: 534.398 kcal/mol).

Furthermore, the other methyl group relative to H-5" appears in 0.80 ppm coupling with H-3" and H-4" (1.28 ppm; m, 4H) methylene of the alkyl group (COSY data). The alkyl group were detected by the H-1" in 2.55 ppm (dd, J=8.6, 4.9 Hz, 2H) and H-2" in 1.52 ppm from the COSY spectrum (FIG. 11). All of the 1D and 2D $^1$H NMR spectrum information showed that the chromophore compound from $\Delta^9$-THC plus FBBB is in the para position. This is the first time that evidence of FBBB coupling in the para position of $\Delta^9$-THC has been reported in the literature.

The compound isolated from Rf 0.51 presented a $^1$H NMR spectrum similar to the $\Delta^9$-THC plus FBBB linked in the para position, being the major difference in the chemical shift 6.0-6.5 ppm range which corresponds to the para position addition. Due to the impurity of the compound with Rf 0.51 it was not possible to identify the compound with HNMR. In DART(+)MS and DART(+)MS/MS analysis for the compound with Rf 0.51, however, the same ion peak with m/z 626, when compared to the compound with Rf 0.15, suggests that another compound was found in the chromophore of $\Delta^9$-THC with FBBB reaction at this Rf.

Example 7—Theoretical Calculations of the Reaction Coordinate

Figures 26A, 26B, 26C, 26D:
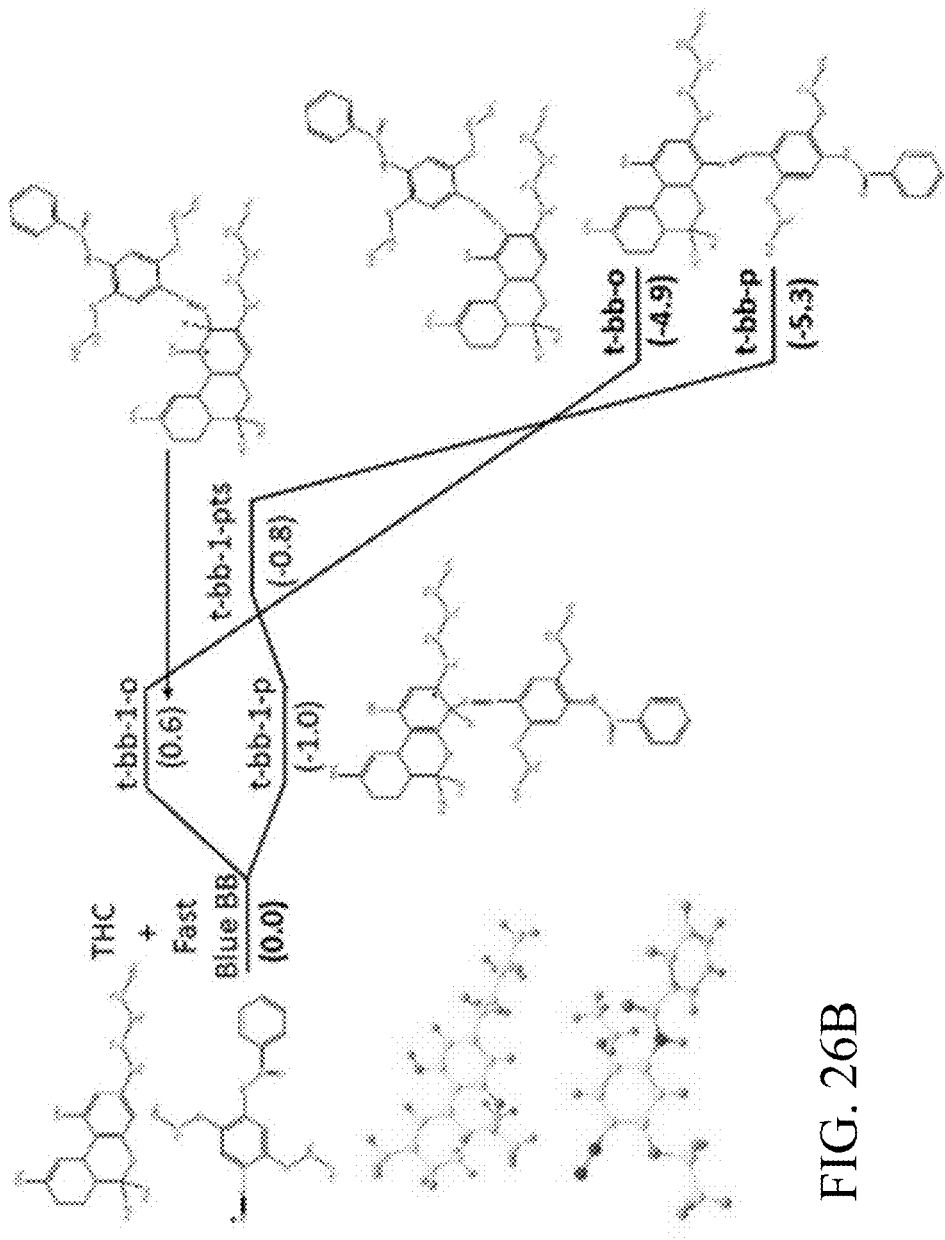
FIGS. 26A-26D show the optimized geometries and the energy profile (in kcal/mol) of the reaction coordinate calculated at the B3LYP/3-21g level of theory of the reactants (depicted in A) THC and B) FBBB), initial addition intermediates (t-bb-1-o/t-bb-1-p), transition state (t-bb-1-pts), and products in the ortho and para (depicted in C) t-bb-o and D) t-bb-p, respectively) pathways.

The reactants, intermediates, transition states, and products from the reactions of $\Delta^9$-THC and FBBB were calculated at the B3LYP/3-21g level of theory (FIGS. 12-25). Here, the reactants enthalpy at 0 K, $\Delta^9$-THC and FBBB, was set at 0 kcal/mol and all of the intermediates, transition states, and products were calculated relative to the energy of the reactants. FIG. 26 gives the optimized structures of the reactants (a for $\Delta^9$-THC and b for FBBB) and the two products from ortho and para additions (c and d, respectively) identified in this study. FIG. 26 also gives the energy profile of the reactants, initial adducts upon addition, transition states leading to products from C—H scission, and the ortho and para addition products of the chromophore. The ESI gives additional intermediates that may exist in the reaction coordinate from 1 to 2, 1-3, or 1-4 hydrogen migration steps, however, the reaction steps leading to these intermediates are not investigated in this study and is left for a future theoretical investigation of all the possible reaction steps in the $C_{38}H_{48}O_5N_3$ PES, including the conformers of each intermediate.

The initial adduct upon addition of FBBB onto THC in the para position (given as t-bb-1-p) is exothermic by 1.0 kcal/mol relative to the energy of the reactants, while the initial adduct in the ortho position (1-bb-1-o) is endothermic by 0.6 kcal/mol relative to the energy of the reactants. The product from the para position (t-bb-p) is exothermic relative to the energy of the reactants by 5.3 kcal/mol, while the product from the ortho position (t-bb-o) is also exothermic, by 4.9 kcal/mol and lying 0.4 kcal/mol above the energy of the para addition product. This 2.6 kcal/mol difference in energies of the initial adducts and 0.4 kcal/mol energy difference of the products, both energetically favoring the para pathway, warrants the greater yield in product formation of the para product over the ortho pathway.

Example 8—GC-MS

A thermal desorption gas chromatography method was used to test out the novel sorbent device, Capillary Microextraction of Volatiles (CMV). CMVs were directly thermally desorbed into a 7890A Gas Chromatograph and 5975C Mass Spectrometer (GC-MS) using a thermal desorption probe (Agilent). Analyte recovery was determined by spiking 1 µL standard solutions onto the CMV (FIG. 27). Instrument parameters are shown in Table 3.

TABLE 3

Instrument parameters.
Optimized GC-MS Parameters

| | |
|---|---|
| GC Inlet | 250° C. Splitless |
| Oven Temperature Program | Initial: 50° C. (2 min hold) Ramp: 10° C./min to 240° C. 5° C./min to 280° C. (7 min hold) |
| GC Column | ZB5-MS 60 meters |
| Gas Flow | 1.5 mL/min |
| Aux Temp | 280° C. |
| MS Quad Temp | 150° C. |
| MS Source Temp | 230° C. |
| Acquisition mode | Fullscan 30-450 m/z |

Figure 28:
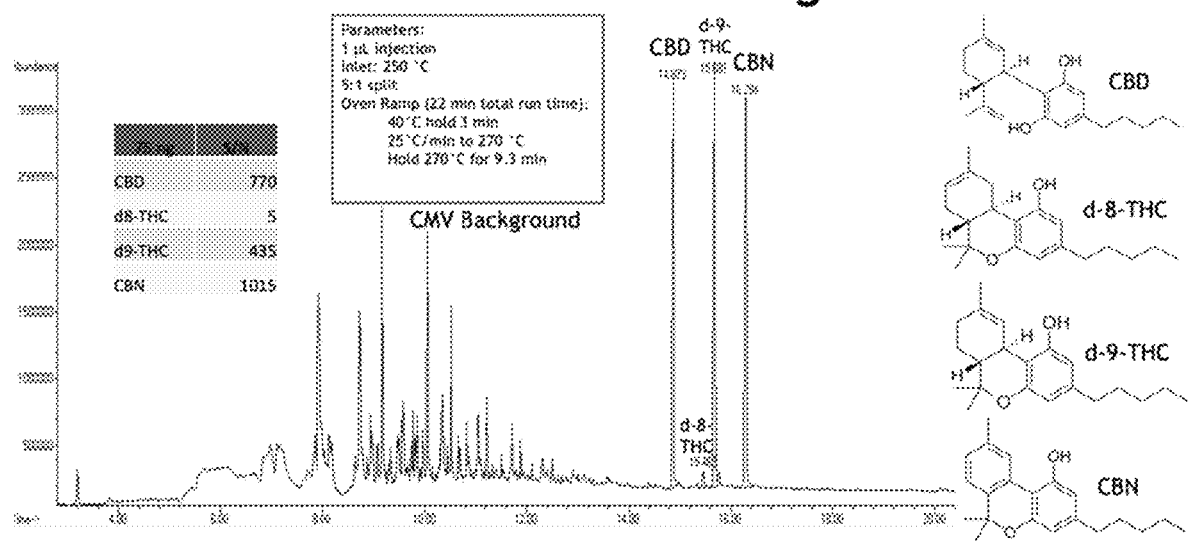
FIG. 28 shows thermal desorption GC-MS analysis of CMV-A strip containing a mixture of 4 cannabinoids (CBD, CBN and $\Delta^8$-THC, $\Delta^9$-THC) at 75 ng mass loadings of each of the analytes.

FIG. 28 illustrates the separation afforded by GC after thermal desorption of CMV-A strip containing a mixture of 3 cannabinoids (CBD, CBN and $\Delta^9$-THC) at 75 ng mass loadings of each of the analytes, illustrating the ability to directly analyze the target analytes by GC-MS using thermal desorption of the CMV substrate with good signal to noise.

Example 9—Optimization of Samples

When sampling cannabis it is important to identify which part of the plants will be tested. This is because different parts of the plant vary in the concentration of cannabinoids. The flowers and buds have the highest concentrations of cannabinoids and are the areas of the plants used for recreational purposes but the entire plant can be sampled, homogenized and sub-sampled. For example, at least one gram of the plant material can be homogenized, and three sub-samples of ~10 mg can be used for the extraction step. Commercially available plant grinders can be used for the homogenization step but other homogenization tools can also be evaluated. ANOVA and design of experiment tools are used to assess homogenization efficiency and note any differences between homogenization methods.

Three 5-15 mg sub-samples of the homogenized plant material can be collected using a commercially available and inexpensive core sampling tool. Different core diameters from 2.0 mm to 8.0 mm can be evaluated to approximate a ~5-15 mg sampling mass with a +/−10% target uncertainty for the mass. Subsamples of 5 mg, 10 mg, and 15 mg mass are extracted in 0.5-1 mL of solvent. Methanol, ethanol, and/or mixtures of solvents such as acetonitrile/methanol (80:20 v/v) can be tested to determine which solvent obtains the best results. The precise (+/−) 10% addition of 10 uL volumes of an extract aliquot and of the base may be used.

The overall goal for this sampling and sample preparation step is to use the smallest amount of plant mass and lowest solvent volumes for extraction that result in reliable color changes. FIG. 29 illustrates the colors formed between FBBB reagent and total $\Delta^9$-THC at different mass loading equivalents from 0 ng to 5000 ng THC using a 5 mg sample of plant extracted with 1 mL of ethanol and depositing 10 uL of the extract into the well. FIG. 30 shows the fluorescence emission associated with the product of the FBBB+$\Delta^9$-THC reaction (red emission with a λmax at 640 nm after 480 nm excitation) in comparison to CBD from a hemp plant extract (no emission) at 5000 ng THC mass loading.

Example 10—Color Determination Using RGB

Currently, once the colors have developed on a CMV substrate, the substrate is scanned and the image is analyzed using imaging software (image J) to obtain an RBG code for the resulting color. Obtaining RGB codes to confirm the color and its intensity decreases the subjective determination that relies on sight and provides more objective data regarding color (and, eventually, intensity). This allows one to obtain numerical values that allow for quantitative figures of merit such as LOD, accuracy and precision. This increases the reliability of the tests potentially making it a semi-quantitative method of analysis.

This procedure may be transferred from a digital scanner and a software on a computer to a mobile device so it can be used readily in the field. If successful, a mobile device may be used to convert an image to a color scale using off-the-shelf apps and be able to determine the concentration of THC or CBD by referring to a color chart that correlate color to concentration of cannabinoids. Once the RBG procedure has been finalized, the analytical figures of merit for the test stripes can be evaluated. The LOD for FBBB and the 4-AP tests can be established visually and through RGB codes.

To evaluate the LODs for the color test, a range of concentrations of THC, CBD, and other cannabinoids can be tested with FBBB and the 4-AP test. The concentration where a color can be determined based on RGB value will be considered the LOD for the test method.

To evaluate the sensitivity and specificity of these test strips the true positive rate (TPR) and true negative rate (TNR) can be calculated. Type I and Type II error rates can be determined by calculating the false positive rate (FPR) and false negative rate (FNR) of the test strips. The test strips can then be used to examine extracts from these samples. The number of true positive results (TP), true negative results (TN), false positive results (FP), and false negative results (FN) will be summed and used to calculate TPR, TNR, FPR, and FNR using the following equations (1-4):

$$TPR = \frac{TP}{TP+FN} \times 100 \quad TNR = \frac{TN}{TN+FP} \times 100 \quad \text{(Equation 1 and 2)}$$

$$FPR = \frac{FP}{FP+TN} \times 100 \quad FNR = \frac{FN}{TP+FN} \times 100 \quad \text{(Equation 3 and 4)}$$

The acceptable criteria for TPR and TNR will be 95% and an FPR and FNR below 5%.

The minimum quantity detectable by the naked eye of the reddish color by reaction fast blue BB and the standard cannabinoids ($\Delta^9$-THC, CBD, and CBN) in three-different strips supports was 50 ng for paper and 100 ng for CMV A and B. The polar fraction of the commercial teas and hop products exhibits no or minimal potential interferent for a colorimetric test with FBBB when the extraction was conducted with a non-polar solvent. When using non-polar solvents, all three industrial hemp products used gave negative results for the FBBB test.

The mass spectrometry analysis with DART/MS showed the formation of the colorimetric products between cannabinoids standard and FBBB in the paper, CMV A and B supports with ion peaks in m/z=626 for $\Delta^9$-THC plus FBBB and CBD plus FBBB as well as m/z 622 for CBN plus FBBB. The best temperature for DART analysis was 400° C. using CMV A or CMV B with no degradation at this temperature. The DART(+)MS/MS analysis, conducted in a Q-TOF with collision-induced dissociation (CID), sheds light on the reaction of the cannabinoids and FBBB. Furthermore, CID in 30 V provided additional information about the fragmentation of the chromophore product including that the fragments originated from the FBBB portion of the chromophore.

The reaction between FBBB and $\Delta^9$-THC resulted in products that could be separated by TLC, producing two intense red color bands with retention factors (Rfs) of 0.15 and 0.51, respectively. After purification and 1D and 2D $^1$H NMR analysis, the compound in Rf 0.15 was identified as $\Delta^9$-THC plus FBBB chromophore linked in the para position. This is the first reporting in the literature that demonstrates the structural confirmation of $\Delta^9$-THC coupled to FBBB, using NMR.

Ab initio calculations at the B3LYP/3-21G level of theory suggest that the intermediates, transition states, and products from the para addition is the energetically favorable pathway versus the ortho addition. All the stationary points from the para addition were lower in energy versus their counterpart stationary points from the ortho addition.

All publications, patents, and patent publications cited are incorporated by reference herein in their entirety for all purposes. The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A colorimetric test strip comprising a series of reaction wells and a series of control wells, each reaction well containing a solid substrate preloaded with a colorimetric reagent that differentiates tetrahydrocannabinol (THC) from other cannabinoids, each control well containing the solid substrate that is not preloaded with the colorimetric reagent, and the solid substrate comprising one or more sorbents selected from polydimethylsiloxane (PDMS), sol-gel PDMS, phenyl-modified PDMS (PhPDMS), carbowax/polyethylene glycol (CW/PEG), carbowax/templated resin (CW/TPR), carboxen/polydimethylsiloxane (CAR/PDMS), divinylbenzene, carbowax, polyacrylate (PA), divinylbenzene/carboxen/polydimethylsiloxane (DVB/CAR/PDMS), carboxen, and polydimethylsiloxane/divinylbenzene (PDMS/DVB).

2. The colorimetric test strip of claim 1, the solid substrate being a capillary microextractor of volatiles (CMV) device comprising a housing having at least two orifices and a sorbent-coated glass microfiber substrate material located in the housing between the at least two orifices, the sorbent comprising at least one of PDMS, sol-gel PDMS, PhPDMS, CW/PEG, CW/TPR, CAR/PDMS, divinylbenzene, carbowax, PA, DVB/CAR/PDMS, carboxen, and PDMS/DVB.

3. The colorimetric test strip of claim 2, the housing being a glass tube.

4. The colorimetric test strip of claim 2, the sorbent comprising PDMS, or PhPDMS.

5. The colorimetric test strip of claim 2, the sorbent-coated glass microfiber substrate material comprising a film of a polydimethylsiloxane gel (PDMS gel) on a plurality of glass microfibers.

6. The colorimetric test strip of claim 1, the colorimetric reagent comprising Fast-Blue BB (FBBB).

7. The colorimetric test strip of claim 1, further comprising a second series of reaction wells, each reaction well in the second series containing a second colorimetric reagent.

8. The colorimetric test strip of claim 7, the second colorimetric reagent comprising 4-aminophenol (4-AP).

9. The colorimetric test strip of claim 1, the one or more sorbents comprising PDMS, and/or PhPDMS.

10. A colorimetric field test kit comprising the colorimetric test strip of claim 1, at least one color chart, a base, an instruction and one or more measuring tools.

11. The colorimetric field test kit of claim 10, the base being NaOH.

12. The colorimetric field test kit of claim 10, further comprising a solvent.

13. The colorimetric field test kit of claim 12, the solvent being methanol, ethanol, methylene chloride, or water.

14. A method for identifying marijuana or hemp in a sample comprising:
contacting the sample with the colorimetric test strip of claim 1,
adding a basic solution to the colorimetric test strip; and determining marijuana and/or hemp in the sample based on a color generated from a reaction between the sample and the colorimetric test strip, wherein a deep red color is indicative of marijuana in the sample and an orange color is indicative of hemp in the sample.

15. The method of claim 14, the sample being a plant extract.

16. The method of claim 14, the basic solution being NaOH.

17. The method of claim 14, further comprising a confirmation step comprising inserting each solid substrate of the colorimetric test strip into an injection port of an analytical device configured to separate, detect, and identify at least one component of the sample; and determining from the detected and identified at least one component of the sample marijuana and/or hemp in the sample.

18. A method for identifying tetrahydrocannabinol (THC), cannabidiol (CBD) and/or cannabinol (CBN) in a sample comprising:
 contacting the sample with the colorimetric test strip of claim 1,
 adding a basic solution to the colorimetric test strip; and
 determining THC, CBD and/or CBN in the sample based on a color generated from a reaction between THC, CBD and/or CBN and the colorimetric test strip, wherein a deep red color is indicative of THC in the sample, an orange color is indicative of CBD in the sample, and a purple color is indicative of CBN in the sample.

19. The method of claim 18, the basic solution being NaOH.

20. The method of claim 18, the sample being a plant extract or a fluid sample from a subject.

* * * * *